United States Patent [19]
Rakhmilevich et al.

[11] Patent Number: 5,922,685
[45] Date of Patent: Jul. 13, 1999

[54] IL-12 GENE THERAPY OF TUMORS

[75] Inventors: Alexander L. Rakhmilevich, Delafield; Ning-Sun Yang, Verona, both of Wis.

[73] Assignee: Powderject Vaccines, Inc., Madison, Wis.

[21] Appl. No.: 08/659,206

[22] Filed: Jun. 5, 1996

[51] Int. Cl.[6] .......................... A61K 48/00; C12N 15/00; C12N 15/87
[52] U.S. Cl. .......................... 514/44; 435/320.1; 435/459
[58] Field of Search .............................. 514/44; 536/23.1; 424/93.2, 93.21; 435/320.1, 172.3; 935/52, 56

[56] References Cited

U.S. PATENT DOCUMENTS

| | | |
|---|---|---|
| 4,945,050 | 7/1990 | Sanford et al. . |
| 5,015,580 | 5/1991 | Christou et al. . |
| 5,149,655 | 9/1992 | McCabe et al. . |

FOREIGN PATENT DOCUMENTS

| | | |
|---|---|---|
| WO 94/16716 | 8/1994 | WIPO . |
| WO 95/19799 | 7/1995 | WIPO . |

OTHER PUBLICATIONS

Vieweg et al (1995) Clinical Invest. 13, 193–201.
Vieweg et al. (1994) Cancer Res. 54, 1760–1765.
Xu et al. (1997) Vaccine 12, 1534–1536.

Gubler et al., "Coexpression of Two Distinct Genes is Required to Generate Secreted Bioactive Cytotoxic Lymphocyte Maturation Factor," *Proc. Natl. Acad. Sci. USA* 88:4143–4147 (1991).

Lotze et al., "Gene Therapy of Cancer–Immunological Approaches," *J. Cellular Biochemistry* S17E: p. 184 (1993).

Lotze, Michael T., "Cytokine Gene Therapy of Cancer–IL–4 and IL–12 Regulate the Immune Response," *Cancer Gene Therapy* (Conference Abstracts) 1:(2) 147–148 (1994).

Martinotti et al., "CD4 T Cells Inhibit In Vivo the CD8–Mediated Immune Response Against Murine Colon Carcinoma Cells Transduced with Interleukin–12 Genes," *Eur. J. Immunol.* 25:137–146 (1995).

Robbins et al., "Gene Therapy for Cancer and Arthritis," *Cancer Gene Therapy* (Conference Abstracts) 1(2):p.147 (1994).

Tahara et al., "Fibroblasts Genetically Engineered to Secrete Interleukin 12 Can Suppress Tumor Growth and Induce Antitumor Immunity to a Murine Melanoma in Vivo," *Cancer Research* 54:182–189 (1994).

*Primary Examiner*—Deborah Crouch
*Attorney, Agent, or Firm*—Robins & Associates; Thomas P. McCracken

[57] ABSTRACT

In an approach to genetic therapy for treating tumors, a genetic construction encoding the p35 and p40 subunits of the cytokine IL-12 is delivered into cells of individuals in need of therapy so as to express IL-12 in cells and to cause regression of established tumors.

15 Claims, 5 Drawing Sheets

5,922,685

IL-12 GENE THERAPY OF TUMORS

FIELD OF THE INVENTION

The present invention relates generally to the field of treatment of tumors, and relates in particular to the direct delivery into skin cells of a genetic construct containing the IL-12 gene.

BACKGROUND OF THE INVENTION

Interleukin (IL) 12, formerly termed natural killer cell-stimulatory factor or cytotoxic lymphocyte maturation factor, is a disulfide-linked heterodimeric cytokine composed of 35-and 40-kDa subunits; the subunits are commonly designated "p35" and "p40". The complimentary DNAs encoding the p35 and p40 subunits from both the mouse and humans have been sequenced and cloned, and both human and mouse IL-12 have been shown to act as growth factors for natural killer ("NK") cell and T-cell, in vitro and in vivo. Furthermore, IL-12 has also proven to be effective in regression and complete disappearance of murine tumors. Tahara et al., *Cancer Research* 54 (1): 182–9, 1994; Brunda et al., *J. EXP. MED.* 178 (4): 123–30, 1993.

However, because IL-12 has a short half life in vivo, frequent injections of the cytokine are needed to achieve therapeutic effects. Moreover, relatively large quantities of IL-12 (in the range of 1–10 μg/day) are typically required. Therefore, administration of recombinant IL-12 often resulted in toxicity.

IL-12 gene therapy using retroviral vectors is underway in several laboratories, and its anti-tumor effect has been demonstrated. Lotze, M. T., et al., *J. Cell. Biochem., p.*184, 1993.; Robbins, et al., *Cancer Gene Therapy* 1(2):147, 1994. In the Lotze, et al. study, the genes for IL-12 p35 and p40 subunits were inserted into NIH 3T3 fibroblasts. The fibroblasts were used to deliver IL-12 at the site of tumors, delaying growth of a variety of murine tumors. In the Robbins, et al. study, the direct delivery of IL-12 to several different mouse tumor lines by retroviral-mediated transduction prior to inoculation or to fibroblasts that were then coadministered with tumor cells resulted in inhibition of tumor growth as well as in the induction of antitumor immunity.

However, to date, it was not possible to cause reliable regression of established tumors and their spontaneous metastases using direct IL-12 gene therapy.

SUMMARY OF THE INVENTION

The present invention is summarized in that an anti-tumor response can be effected after transfer to a mammalian animal of a DNA molecule that encodes the cytokine IL-12.

In one aspect the invention is a method to treat tumors in an animal, preferably a mammal and most preferably a human, by genetic therapy. In the method, copies of a foreign genetic construction are prepared. The genetic construction includes a promoter operative in cells of the animal and protein coding regions encoding both the p35 and p40 subunits of the cytokine IL-12. The foreign genetic construction is then physically delivered into the epidermis of the tumor-bearing animal in need of such genetic therapy.

In another aspect, the invention provides a genetic construct for treating tumors. The construct is provided by operatively joining DNA sequences encoding the p35 and p40 subunits of the cytokine IL-12 to a promoter effective in the animal's cells. The construct is suitable for transduction into cells of an animal by, for example, a particle-mediated transfection process.

It is an object of the present invention to enable the treatment of tumors through the use of an IL-12 genetic construct.

It is a feature of the present invention in that it is adapted to either epidermal or mucosal delivery of the genetic construct.

It is an advantage of the genetic treatment of the present invention that it is inherently safe, not painful to administer, and should not result in adverse consequences to treated individuals.

It is a further advantage of the genetic treatment of the present invention that the genetic treatment is effective even when delivered to a site distant from the tumor, and immunological memory is retained after genetic treatment ceases.

Other objects, advantages and features of the present invention will become apparent from the following specification.

DETAILED DESCRIPTION OF THE INVENTION

Figure 1:
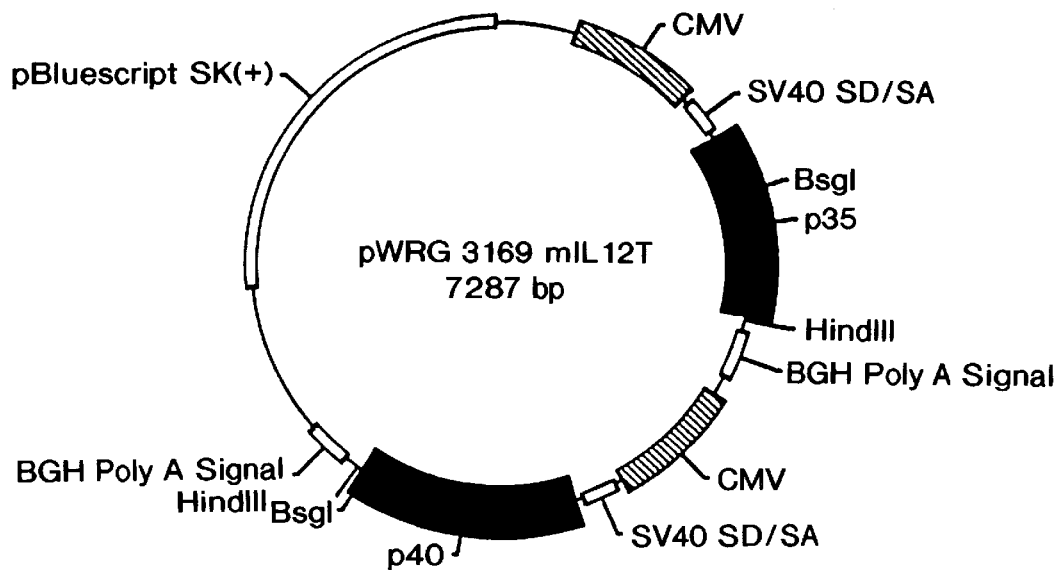
FIG. 1 is a plasmid map of the IL-12 plasmid pWRG3169.

The present specification describes a method to treat tumors by delivering a genetic construct encoding the p35 and p40 subunits of IL-12 protein into the epidermis of a patient at the tumor site. The tumors can be solid tumors or metastatic or disseminated tumors, and can be microscopic or visible with the naked eye. Once the construct is delivered, the heterodimeric IL-12 cytokine is expressed, resulting in the creation of an anti-tumor response in treated individuals, even when the tumor is far removed from the delivery site.

In order to achieve the genetic treatment sought of the present invention, an IL-12 genetic construction is created in which the IL-12-encoding genes are placed under the control of a promoter operative in the cells of a target mammalian animal. When transfected into cells of a treated animal, a suitable construct causes expression of the IL-12 protein.

IL-12 protein is actually a heterodimer that includes a 35 kDa (p35) and a 40 kDa (p40) subunit. Each subunit is encoded by a distinct gene. The IL-12 p35- and p40-encoding DNA sequences can be obtained or derived from a mammalian animal source, preferably from a human source. A full-length DNA sequence encoding human IL-12 subunits has been published by Gubler, et al., *Proc. Natl. Acad. Sci. USA* 88: 4143–4147, 1991. The published human nucleic acid and amino acid sequences of a p35 subunit are available at GenBank Accession number M65271. Similarly, the nucleic acid and amino acid sequences of a human p40 subunit are also available at GenBank Accession number M65272.

Alternatively, the IL-12 subunit-encoding sequences can be obtained from any other non-human animal that produces IL-12. The IL-12 subunit-encoding sequences may be obtained or derived from other species which demonstrate sufficient sequence identity to be functionally equivalent to human IL-12. For example, IL-12 is known to be produced by mice. Mice sequences were used in the example constructs reported herein. A p35-encoding DNA is reported at GenBank Accession number M86672. The p40-encoding DNA is also available from GenBank.

Also, in vitro-synthesized coding sequences encoding IL-12 p35 and p40 subunits can readily be prepared in quantities sufficient for molecular cloning using standard recombinant molecular biological techniques, including PCR amplification and hybridization, using the published DNA sequence as a guiding template.

It may also be possible to further modify the subunit-encoding DNA molecules and protein subunits disclosed herein, while still maintaining the antitumor activity of the present invention. The present invention is intended to include truncated natural IL-12 DNA having the nucleic acid sequences described herein, as well as all altered, varied and modified forms of the DNA. These can include, but are not limited to substantially homologous DNA fragments having additions, deletions, and point mutations, relative to the disclosed nucleic acid sequences including truncation at the 5' and/or 3' end. A substantially homologous DNA fragment is one wherein the fragment encodes a polypeptide that exhibits significant antitumor activity and/or regression after delivery, even if such DNA differs in nucleic acid sequence or encodes a protein that differs in amino acid sequence from the DNA fragments or proteins disclosed herein. Anti-tumor activity of such truncated DNA molecules can be monitored as described below.

One skilled in the art will recognize that certain silent changes to the nucleic acid sequence have no effect on the amino acid encoded by a particular triplet. Even certain amino acid changes that do not affect, or only somewhat affect, the IL-12 activity of the encoded protein may be used within the scope of the invention. Any nucleic acid or amino acid sequence that results in anti-tumor activity that is at least 75% of the activity obtained using the murine IL-12 (mIL-12) genes tested as described in the following Examples may be used in the present invention.

Of course, if the gene encoding an IL-12 protein is engineered into a genetic construct for delivery into a host of a species other than that from which the gene derives, an immune response may occur after gene transfer. However, one skilled in the art will understand that by modifying the nucleic acid sequence of the mature IL-12 portion of the delivery gene, it is possible to eliminate such effect.

To properly express the IL-12 subunit genetic sequences in transfected cells, a promoter sequence operable in the target cells is needed. Several such promoters are known for mammalian systems which may be joined 5', or upstream, of the coding sequence for the protein to be expressed. A preferred promoter is the CMV promoter, the sequence of which is well known and which has been published at Cell, 41:521–530 (1995). A downstream transcriptional terminator, or polyadenylation sequence, may also be added 3' to the protein coding sequence. A preferred polyadenylation sequence is the bovine growth hormone poly A region, the sequence of which is known. Splice donor and splice acceptor (SD/SA) sites, such as the SV40 SD/SA, may also be positioned in the construct if desired, as may an internal ribosome entry site (IRES), such as the IRES cloned from encephalomyocarditis virus.

As the inventors describe in more detail in the Examples, below, it has been determined that expression of the two protein-encoding sequences from separate transcription units on a single plasmid results in significantly higher protein levels than are observed when bicistronic expression of the genes is driven from a single promoter. Thus, for purposes of this invention, it is preferred that each coding region be provided with a separate promoter.

Introduction of the Genetic Material

In the present invention, a suitable genetic construct encoding IL-12 protein subunits is transferred into the susceptible individual. A genetic treatment can be delivered in a non-invasive manner to a variety of susceptible tissue types in order to achieve the desired immunological response in the individual.

It is herein disclosed that when treating tumors with the IL-12 genetic construct, the preferred target cells are epidermal cells rather than cells of deeper skin layers such as the dermis. Epidermal cells are preferred recipients of the IL-12 genetic construct because they are the most accessible cells of the body. Patients in need of such genetic therapy may advantageously, therefore, be treated non-invasively. Moreover, quite unexpectedly, and contrary to what some might think, epidermal delivery of the IL-12 gene successfully treats tumors far removed from the delivery site, and furthermore, generates systemic anti-tumor immunity, immunological memory, and cytotoxic responses. Therefore, epidermal delivery is well particularly suited for non-invasive delivery of the IL-12 genes.

Inasmuch as IL-12 genetic construct treatment has proven successful in eliciting successful anti-tumor responses following gene gun-based IL-12 genetic construct delivery to the skin, it is also probable that non-invasive delivery of the IL-12 genetic construct to mucosal surfaces will result in successful treatment responses as well.

It is also specifically envisioned that aqueous droplets containing naked IL-12 DNA can be delivered directly into the tissues of the individual sought to be treated. At some frequency, such "naked" DNA will be taken up in the treated tissues.

The preferred transfer means for non-invasive delivery is an accelerated particle gene transfer device, although any means that can reliably transfer the construct into the suitable target sites (epidermis or mucosal tissue) is acceptable. The technique of accelerated-particle gene delivery is based on the coating of genetic constructions to be delivered into cells onto extremely small carrier particles, preferably gold particles, which are designed to be small in relation to the cells sought to be transformed by the process. The gold particles may be beads or spheres or amorphous gold. All are suitable for use in the present invention. Reference herein to particles is intended to include all such forms. Amorphous gold, such as Englehard microcrystalline gold, has been demonstrated in other biological target systems to achieve higher delivery into target cells than other types of gold.

Without regard to the type of particle acceleration apparatus or suitable particles used, the coated carrier particles are then physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in procaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. The accelerated particle method is also preferred in that it allows a genetic treatment construction to be directed both to a particular tissue, and to a particular cell layer in a tissue, by varying the delivery site and the force with which the particles are accelerated, respectively.

The general approach of accelerated particle gene transfection technology is described in U.S. Pat. No. 4,945,050 to Sanford, incorporated herein by reference. An instrument based on an improved variant of that approach is available commercially from BioRad Laboratories. An alternative approach to an accelerated particle transfection apparatus is disclosed in U.S. Pat. No. 5,015,580, herein incorporated by reference, which, while directed to the transfection of soybean plants, describes an apparatus which is equally adaptable for use with mammalian cells and intact whole mammals. U.S. Pat. No. 5,149,655, incorporated herein by reference, describes a convenient hand-held version of an accelerated particle gene delivery device. Other such devices can be based on other propulsive sources using, for example, compressed gas as a motive force.

Gene gun delivery allows for precise control over the level and form of IL-12 production in a given epidermal site because intracellular DNA delivery can be controlled by systematically varying the number of particles delivered and the number of plasmid copies per particle. This precise control over the level and form of cytokine production may allow for control over the nature of the resultant response.

The term transfected is used herein to refer to cells which have incorporated the delivered foreign IL-12 genetic construction, whichever delivery technique is used. The term transfected is used in preference to the term transformation, to avoid the ambiguity inherent in the latter term, which is also used to refer to cellular changes in the process of oncogenesis.

The present invention will be more fully understood by reference to the following examples, which are intended to be merely exemplary of the invention. In the examples, mice have been used as a model recipient for the IL-12 expression construct. Mice are the standard animal model for extrapolation to human tumors, and general FDA policy requires researchers to demonstrate efficacy of a proposed cancer treatment in mouse models before undertaking clinical trials.

EXAMPLES

Construction of Plasmids Encoding murine IL-12

Two murine IL-12 constructs have been used, each of which encodes both the p35 and the p40 subunits of mIL-12. These subunits were cloned from a mouse spleen cDNA library. All plasmids were made with the express purpose of increasing cytokine gene expression of IL-12, and with the immediate intended use in a cancer gene therapy program.

Plasmid pWRG3169 is a tandem plasmid encoding both mIL-12 subunit genes. A map of plasmid pWRG3169 is provided in FIG. 1 and the complete nucleotide sequence of the plasmid is presented in SEQ ID NO:1. The p35 and p40 products of the plasmid are reported as SEQ ID NO:2 and SEQ ID NO:3, respectively. Each subunit-encoding gene is under the transcriptional control of a separate cytomegalovirus (CMV) promoter. An SV40 splicing donor/splicing acceptor (sa/sd) is provided between each subunit-encoding segment and its CMV promoter. Just downstream (3') to each subunit-encoding segment is a bovine growth hormone polyadenylation signal (bGH pA). Each unit (promoter—sa/sd—coding region—poly A signal unit) is transcribed in series (i.e., in the same direction) from the plasmid. The pUC19 plasmid backbone is derived from a Bluescript® SK(+) vector with an ampicillin resistance gene which is available commercially from Stratagene Cloning Systems, La Jolla, Calif.

Figure 2:
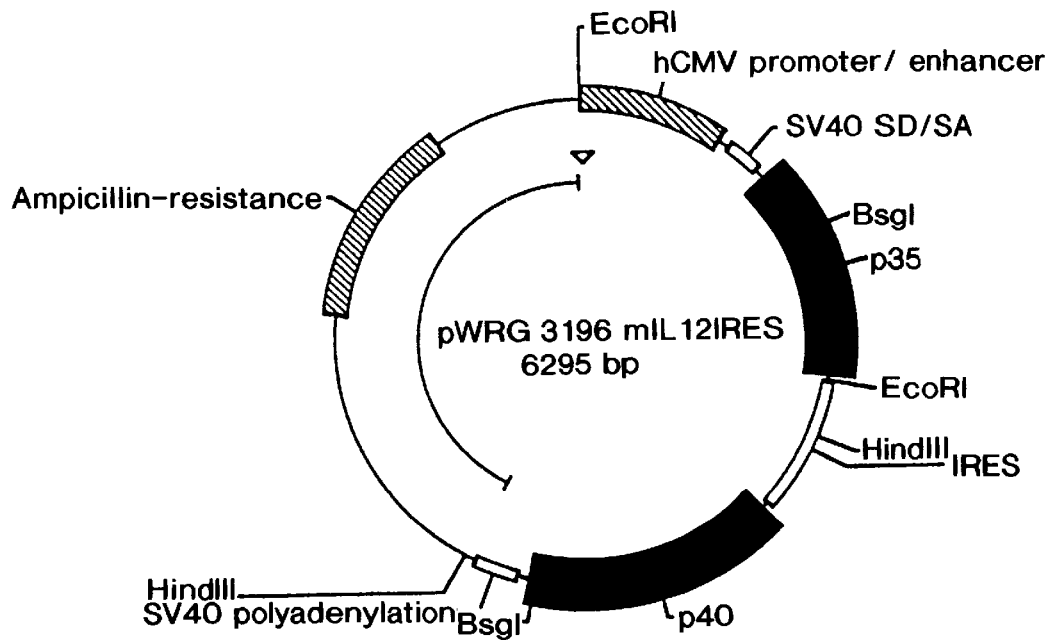
FIG. 2 is a plasmid map of the IL-12 plasmid pWRG3196.

Plasmid pWRG3196 is a bicistronic plasmid encoding both subunits of mIL-12. A map of plasmid pWRG3196 is provided in FIG. 2 and the complete sequence is shown in SEQ ID NO:4. The p35 and p40 products of the plasmid are reported as SEQ ID NO:5 and SEQ ID NO:6, respectively. The pUC19 plasmid backbone was derived from a Bluescript SK(+) vector with an ampicillin resistance gene. This vector contains a single cytomegalovirus (CMV) promoter, SV40 splicing donor/splicing acceptor, and bovine growth hormone polyadenylation signal. Both the p35 and p40 genes are provided downstream from the sd/sa site and upstream from the SV40 poly A site. The p35 gene is upstream from (i.e., closer to the promoter than) the p40 gene. Between the p35 and p40 genes is an internal ribosome entry site element (IRES) cloned from encephalomyocarditis virus. The IRES element is a non-coding region which functions as an internal entry point for initiation or continued translation by eukaryotic ribosomes.

Both pWRG3169 and pWRG3196 direct expression of mIL-12. From a molecular standpoint, however, the bicistronic IRES vector (pWRG3196) produces a single mRNA, whereas the tandem vector (pWRG3169) produces separate mRNA for p35 and p40. In gene expression studies, the present inventors discovered that pWRG3169 induced at least twice the expression of the bicistronic pWRG3196, both in vivo and in vitro. For example, when the pWRG3169 and pWRG3196 vectors were transfected separately into B16 tumor cells in vitro, or into murine skin in vivo, 3–8 fold higher mIL-12 protein expression levels were observed when the pWRG3169 vector was transfected. Still lower expression levels were observed when two separate vectors, each encoding one of mIL-12 subunit proteins, were transfected.

Importantly, biologically active IL-12 cytokine was detected locally after transfer to B16 murine melanoma cells and after skin bombardment using a particle acceleration instrument. When 1.25 $\mu$g of pWRG3169 DNA was delivered by particle acceleration into $1 \times 10^6$ B16 cells, 49.8±10.2 ng/ml were detected after 24 hours. Twenty-four hours after skin was bombarded four times with a total of 5 $\mu$g of pWRG3169 DNA, 266±27.8 pg of IL-12 were detected per 0.172±0.026 gm of tissue in a standard $1.5 \times 1.5$ cm$^2$ full thickness skin biopsy which contained four treated sites. The level of IL-12 was determined using a cell proliferation assay using murine Con-A-activated splenocytes as described by Schoenhaut, et al., *J. Immunol.* 148:3433 (1992).

It is envisioned that similar expression-competent vector constructs can be created which will include human p35 and human p40, the sequence of which are provided herein) for use in cancer gene therapy clinical studies. In addition, future vectors will include Intron A and possibly an episomal element such as EBNA-1 from Epstein-Barr virus.

Implantation of Tumors in Mice

Renal cell adenocarcinoma (Renca) and methylcholanthrene-induced fibrosarcoma (MethA) tumor cell lines, are syngeneic in Balb/c mice. L5178Y lymphoma and P815 mastocytoma are syngeneic in DBA/2 mice. SA-1 sarcoma and B16 melanoma are syngeneic in A/Sn and C57Bl/6, respectively. Tumor cell lines were maintained in vitro under established conditions.

To induce tumor formation, suitable recipient mice were shaved in their abdominal area and were injected with 1×10⁶ tumor cells in 50 μl of PBS intradermally (except 10⁵ B16 cells were delivered). Tumor growth was monitored 2–3 times a week by measuring two perpendicular tumor diameters using calipers.

Use of mIL-12 Plasmids in Tumor Treatment

The experiments utilized a helium-pulse particle acceleration device of the type described in published PCT application number PCT/US95/00780 (Publication number WO 95/19799), which is incorporated herein by reference. Plasmid DNA was precipitated onto 2 micron gold particles using PEG/CaCl$_2$ or spermidine/CaCl$_2$. Particles were suspended in a solution of 0.1 mg/ml polyvinylpyrrolidone in absolute ethanol. This DNA/gold particle preparation was coated onto the inner surface of Tefzel tubing as described in the incorporated published application. The tubing was then cut into cartridges of 0.5 inch length, to achieve delivery of 0.5 mg gold and 1.25 μg plasmid DNA per bombardment with a single cartridge.

The deposited DNA-coated particles were lifted from the cartridges and were delivered into mouse epidermis under the force of a 300 psi helium pulse. Histologic examination and standard immunohistochemical analyses using a monoclonal anti-IL-12 antibody demonstrated that under this force, the gold particles primarily penetrated to the epidermal cell layers of the mouse skin tissue, but did not penetrate into the underlying tumor cells, and, likewise, that transgenic mIL-12 was expressed only in epidermal cell layers.

At each transfection timepoint, individual mice received four bombardments with the mIL-12 DNA genetic construct or with control DNA (pCMVLuc; Cheng, et al., 90 *Proc. Natl. Acad. Sci. USA* 4455 (1993)). One bombardment was directly over the tumor, and three additional bombardments were evenly spaced around the circumference of the tumor in a triangle pattern.

Regression of Murine Renca and MethA Tumors in Mice

Balb/c mice were inoculated as described above with 1×10⁶ Renca or MethA tumor line cells. At the indicated time after inoculation, the tumor injection sites were bombarded once per day for 3–5 days with pWRG3196, with pWRG3169 or with control plasmid pCMVLuc, starting on day 7 of tumor growth (in the first experiment, bombardment started on days 1, 4, or 7 of tumor growth).

Figure 3:
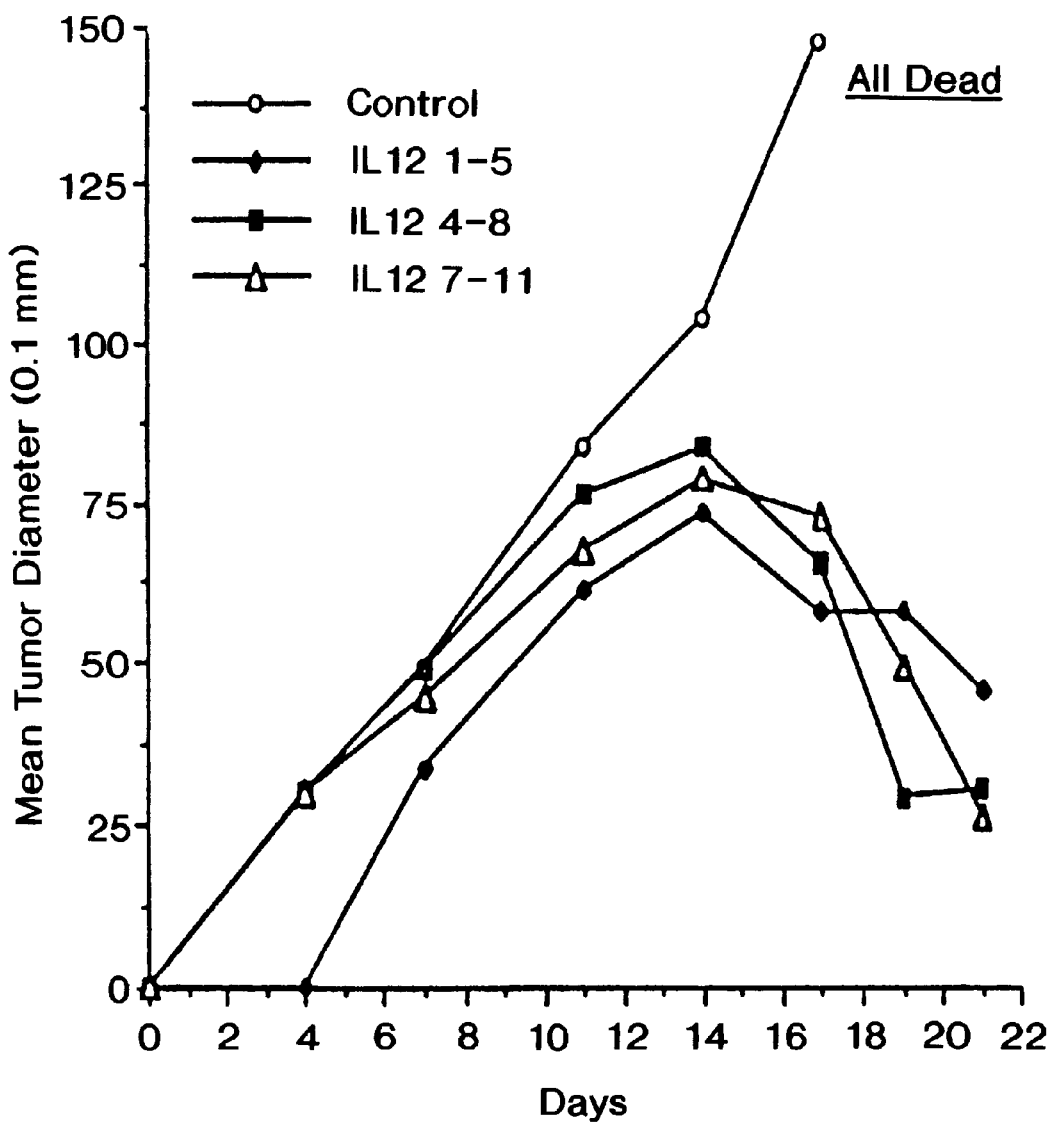
FIG. 3 is a graph presenting tumor growth patterns in IL-12 gene-treated and control mice.
Figure 4A:
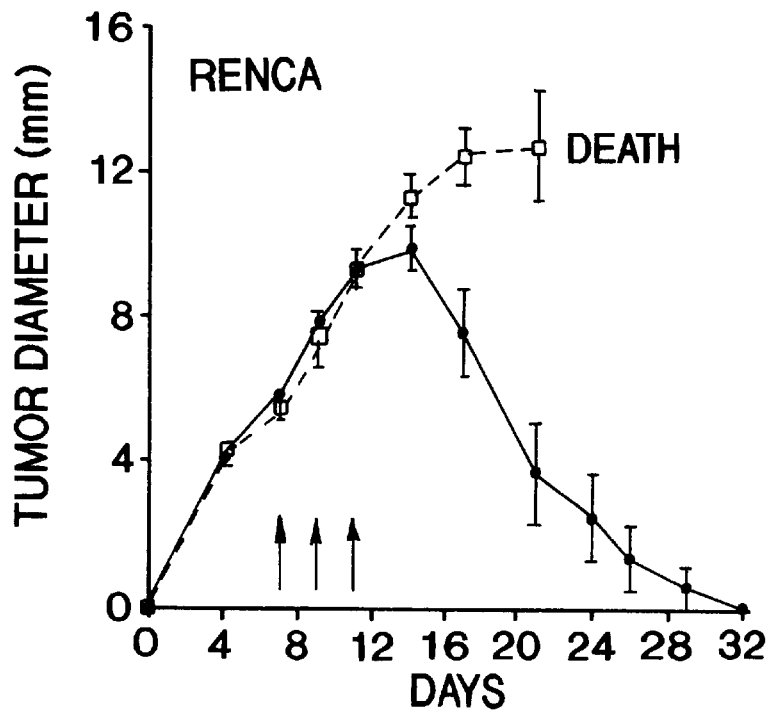
FIGS. 4A–4F are graphs presenting change in diameter of various induced solid tumors after treatment using IL-12 genes.
Figure 4B:
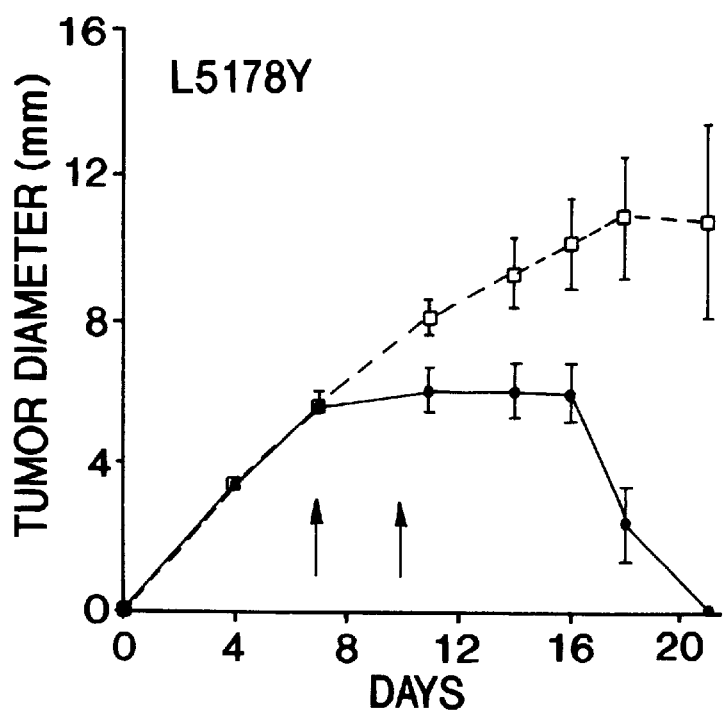
Figure 4C:
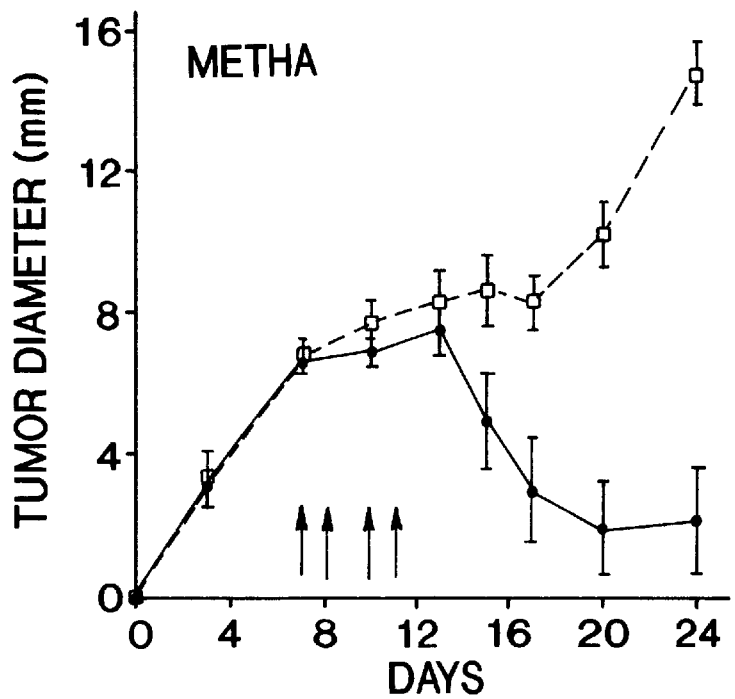
Figure 4D:
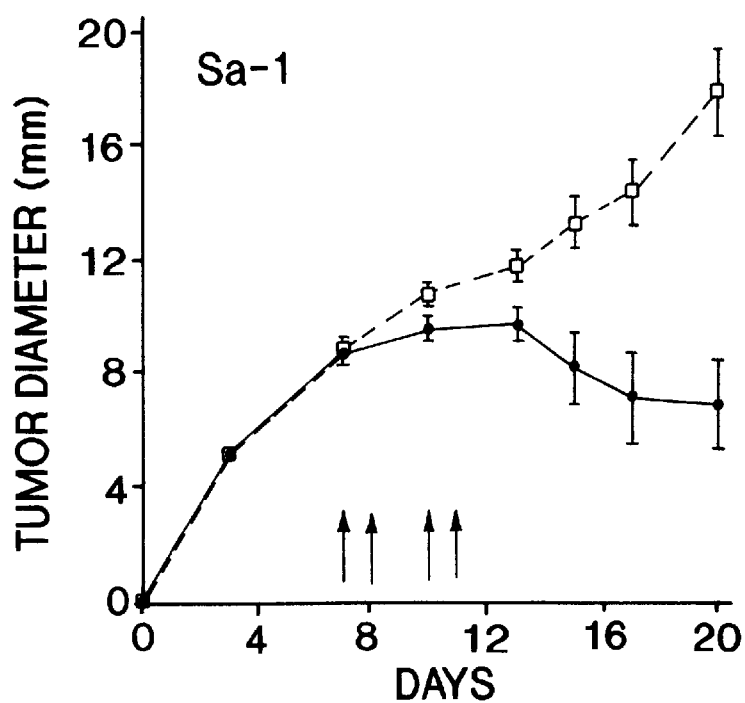
Figure 4E:
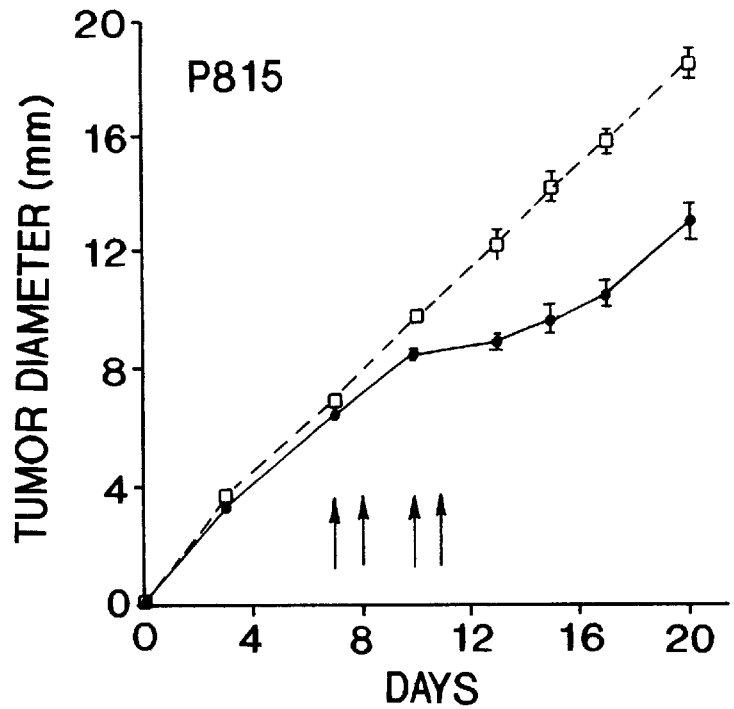
Figure 4F:
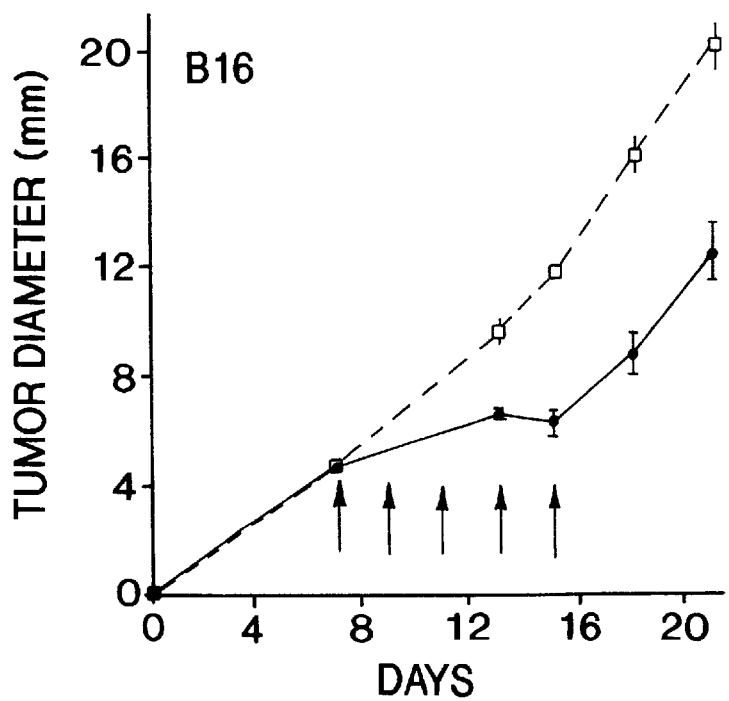

The results of four preliminary experiments are presented in Table 1. In the first experiment, 3 of 7 (42%), 3 of 6 (50%), and 5 of 7 (71%) mice treated on days 1–5, 4–8, and 7–11, respectively, completely rejected their tumors, whereas all control (untreated) mice were sacrificed by day 18 due to progressive tumor growth. The tumor growth pattern in IL-12 gene-treated and control mice is presented in FIG. 3.

It can be seen that regression started several days after terminating the treatment, suggesting that the anti-tumor effect is immunologically-mediated. Moreover, it is important to note that in this and other experiments, in situ bombardment with the mIL-12 encoding plasmid caused regression of established (5–10 mm in diameter) solid murine tumors.

In the second experiment, mIL-12 treatment caused rapid regression in the tumors in all mice. Due to the heavy skin bombardment, however, 28% of mice transfected with the control gene also rejected their tumors. In order to eliminate this nonspecific and anti-tumor effect, the duration of the treatment was reduced to three bombardments every other day.

Indeed in the third experiment, all tumors bombarded with the control gene grew progressively, whereas 62% of mice bombarded with the mIL-12 genetic construct rejected their tumors.

In experiment 4, MethA sarcoma was used instead of Renca tumor and showed similar high sensitivity to IL-12 gene treatment.

TABLE 1

Rejection of intradermal murine tumors following IL-12 gene therapy

| Experiment | Tumor | Treatment/ Days | No. of mice tumor-free/ total | Rejection (%) |
|---|---|---|---|---|
| 1 | Renca | None | 0/7 | 0 |
|   |       | pIL-12$^a$/1–5 | 3/7 | 42 |
|   |       | pIL-12$^a$/4–8 | 3/6 | 50 |
|   |       | pIL-12$^a$/7–11 | 5/7 | 71 |
| 2 | Renca | pCMVLUC/7–11 | 2/7 | 28 |
|   |       | pIL-12$^b$/7–11 | 7/7 | 100 |
| 3 | Renca | pCMVLUC/7,9,11 | 0/8 | 0 |
|   |       | pIL-12$^b$/7,9,11 | 5/8 | 62 |
| 4 | MethA | pCMVLUC/ 7,8,10,11 | 1/8 | 12 |
|   |       | pIL-12$^b$/ 78, 10, 11 | 6/8 | 75 |

$^a$pWRG3196 (IRES); $^b$pWRG3169 (Tandem)

Additional demonstrations of tumor regression

The present inventors also used the IL-12 treatment method of the present invention with other murine tumors, as described below. In all cases, reduction of tumor growth was observed following mIL-12 gene transfection.

It is known that certain murine immunogenic tumors can induce a T cell-mediated immune response which is best detected on days 7–9 of tumor growth in defined tumor models (17). Therefore mIL-12 cDNA treatments were begun at 7 days post-implantation of tumor cells, to enhance the already activated endogenous antitumor immune response. Using this experimental strategy, the in vivo delivery of the chimeric IL-12 genes into skin tissues overlying established 7-day tumors resulted in complete tumor regression or suppression of tumor growth in 4 tumor models. In suitable mice bearing Renca, L5178Y, MethA or Sa-1 tumors, complete tumor regression was achieved in 87.5% (⅞), 87.5% (⅞), 57% (4/7) and 37.5 (⅜) of test mice, respectively. Nearly identical results were achieved with Renca tumors after a single IL-12 cDNA treatment on day 7. The effect of mIL-12 gene therapy on tumor growth in these 4 tumor models are shown in FIG. 4.

Furthermore, in mice bearing P815 mastocytoma or B16 melanoma, a significant suppression of tumor growth was achieved (FIG. 4). For example, on day 13 post P815 tumor cell implantation, the mean tumor diameter in mice treated with pWRG3169 was 8.89±0.27, as opposed to 12.28±0.46 mm for the pCMVLuc control gene in the same expression plasmid (p<0.001). Likewise, on day 15 post B16 tumor cell implantation, tumor diameter in mice treated with pWRG3169 was 6.30±0.045 as opposed to 11.8±0.31 mm for the pCMVLuc control gene plasmid (p<0.001). For these two weakly immunogenic tumor systems, it is unclear whether modified gene transfer regimes or schedules can improve the therapy and result in tumor regression, and this apparently warrants systematic evaluations in future studies.

The mIL-12 gene therapy experiments were repeated 5 times with the Renca tumor system, 4 times with MethA and P815 tumors, 3 times with the B16 tumor, and once with L5178Y tumor model, and similar results were obtained. At each treatment, mice received four transfections with IL-12 DNA (circles) or pCMVLuc DNA (squares). The arrows in FIGS. 4A–4F indicate the days post tumor implantation on which treatment was carried out. Each group contained 7–8 mice, except the B16 tumor model which contained 12 mice per group.

It is important to note that for all tested mouse tumor models, the tumors were already well-established at the beginning of the therapy, and had reached 5–8 mm in diameter. To our knowledge, this is the first evidence that IL-12 gene therapy can cause a complete regression of large, established tumors. Previous studies have shown that IL-12 gene therapy using retroviral vectors resulted in prevention of tumor development, or regression of small, 3-day-old MCA207 sarcomas in 33% of treated mice. It is also noteworthy that only 1–4 days of therapy (using 4 bombardments per tumor site on each day of therapy) resulted in tumor regression or growth suppression in virtually all of our experiments.

In previous studies using recombinant protein therapy, tumor regression required daily injections of IL-12 at doses from 0.1 to 10 $\mu$g for 1 weeks, or 5 days a week for 4 weeks. In conjunction with our previous findings using other cytokine genes, the results presented in FIGS. 1, 2 suggest that transgenic IL-12 production by normal epidermal cells in the vicinity of the tumor can be responsible for the antitumor effect of IL-12 gene therapy.

IL-12 induced Tumor regression involves $CD8^+$ cells

The observed tumor regression depended upon the presence of $CD8^+$ cells. In vivo depletion of $CD8^+$ T cells, but not the depletion of $CD4^+$ T cells, abrogated the effect of mIL-12 gene therapy. To demonstrate this, Balb/c mice were injected intradermally with $1\times10^6$ Renca cells. Skin was transfected with IL-12 or pCMVLuc cDNA expression vectors on days 7, 9 and 11 post tumor implantation. Anti-CD4 mAb (clone GK1.5) or anti-CD8 mAb (clone 2.43), both obtained from Trudeau Institute, Saranac Lake, N.Y., were administered intraperitoneally on days 8 (300 $\mu$g/mouse) and 12 (150 $\mu$g/mouse) after tumor implantation. Control groups included mice that were treated with the IL-12 gene and received rat IgG (Sigma) at the same doses and schedule as the anti CD8-and CD4 mAb, or mice treated with the pCMVLuc gene instead of the IL-12 gene. The anti-CD4 and Anti-CD8 mAb used in this study caused depletion of more than 90% of relevant T cell subsets in mice for 4–days following a single injection. Tumor mass for 8 mice per group continued to enlarge when $CD8^+$ T cells were eliminated, but tumor regression or elimination was observed when $CD4^+$ T cells were removed, or when rat IgG was injected. These data are in agreement with the findings of Brunda et al., J. Exp. Med. 178(4):123–30 (1993) that tumor regression caused by recombinant IL-12 is mediated by $CD8^+$ T cells, but not $CD4^+$ T cells. In fact, depletion of $CD4^+$ T cells with anti-CD4 monoclonal antibody (mAb) appeared to result in slightly accelerated tumor regression, implying that $CD4^+$ T cells may suppress the anti-tumor effect of IL-12 in this tumor model. Indeed, it has been shown that established tumors induce Th2-like $CD4^+$ T suppressor cells, which can inhibit $CD8^+$ T cell-mediated immune responses. The beneficial effect of anti-CD4 mAb treatment for tumor immunotherapy with recombinant IL-2 protein or IL-12 gene has been previously reported. Supporting data show that IL-12 protein can activate tumor-specific $CD8^+$ T cells in vitro, and mediate an anti-suppressive effect on Th2 $CD4^+$ T cells in vivo.

Gene Gun Delivery of the IL-12 Gene into the Tumor Site Causes Systemic Anti-Tumor Effect Resulting in Reduction of Growth of a Distant Tumor The observation that tumor regression caused by local IL-12 gene therapy requires $CD8^+$ T cells suggest that local IL-12 gene delivery might result in a systemic antitumor effect. This hypothesis was tested using the P815 tumor system, in which tumor cells metastasize into the visceral organs several days after the intradermal implantation, thereby causing the death of the mice even when the primary tumor has been surgically removed.

DBA/2 mice were injected intradermally with $1\times10^6$ P815 cells. Skin tissues overlying and surrounding the target tumor were treated with pWRG3169 delivered by particle acceleration (8 mice/group), or pCMVLuc (5 mice/group) on days 12 and 14 after tumor cell implantation. Surgical excision of the tumor was performed on day 15, when tumor size reached about 13 mm in diameter. Additional transfections of control and test constructs into skin on both sides of the abdomen were performed on days 16, 18 and 20 post implantation.

All mice treated with pCMVLuc died in 28.0±0.6 days after tumor cell implantation. Macroscopic examination revealed that death was caused by spontaneous metastases of tumor cells into the internal organs, primarily the liver. mIL-12 gene therapy effectively prolonged the survival of mice (survival time 41.4±4.9 days, p<0.05), and 1 of 8 mice was "cured."

This experiment was repeated without additional transfections post tumor excision, and showed that all of the Luc cDNA treated mice (n=11) died in 43.9±7.1 days, whereas 5 or 12 (41.6%) IL-12 gene therapy-treated mice survived for at least 180 days and thus were considered "cured." These results suggest that local delivery of IL-12 gene into the skin tissues overlying and surrounding the primary tumor can augment systemic antitumor immune response and lead to eradication of established spontaneous metastases.

Balb/c mice were injected intradermally with $10^6$ Renca cells, both in the left and right sides of the abdomen. The tumors on the right side were bombarded with either pWRG3169 or pCMVLuc on days 5, 7, and 9 of tumor growth. IL-12 gene therapy resulted in significant growth reduction in the untreated (left) tumor as compared with the growth of untreated tumors in control mice (tumor diameter on day 22: 9.58±1.82 and 13.18±2.03, respectively; n=8 mice/set, p<0.005). A similar experiment was performed in which the L5178Y tumors on the right side of the abdomen were bombarded with either pWRG3169 or pCMVLuc on days 3 and 6 of tumor growth. In this experimental setting, IL-12 gene therapy resulted in complete tumor regression of the treated (right) as well as untreated (left) tumors in all mice (n=8). An additional experiment has shown that IL-12 gene bombardment of the skin, away from the tumor vicinity, does not affect tumor growth. These results suggest that local activation of immune cells at the tumor site during IL-12 gene therapy generates systemic anti-tumor immunity.

Mice that Rejected the Tumors Following IL-12 Gene Therapy Develop Tumor-Specific Immunological Memory A. Rejection of secondary tumor challenge followed IL-12 gene therapy. Balb/c mice that rejected Renca or MethA tumors following IL-12 gene therapy were injected one month later with $1\times10^6$ of both Renca cells and MethA cells on the right and the left side of abdomen, respectively. As a control, the tumor cells were injected into age-matched naive Balb/c mice (5–8 mice per group).

Mice that rejected intradermal Renca (Group A) or MethA tumors (Group B) following IL-12 gene therapy, or control naive mice, were injected into the right side of the abdomen with Renca cells, and into the left side of the abdomen with MethA cells. Whereas all control mice developed both tumors, mice of Group A developed MethA tumors but not Renca tumors, and vice versa, that is, mice of Group B developed Renca tumors but not MethA tumors.

B. Induction of CTL activity in mice that rejected tumors following IL-12 gene therapy. Tumor-specific CTL were generated in vitro as described by Rakhmilevich et al., *Int. J. Cancer*, 55:338 (1993). Spleen cells ($5 \times 10^6$), derived from Balb/c mice that had rejected Renca tumors due to IL-12 gene therapy and had remained tumor-free for two months, or from age-matched naive mice, were co-cultured with $5 \times 10^4$ mytomicin-C-treated Renca cells in 24-well culture plates in complete RPMI-1640 media. After culturing for 5 days in vitro, graded numbers of viable effector cells and $^{51}$Cr-labeled Renca cells ($10^4$) were placed into the wells of round-bottomed 96-well plates. After incubating for 4 hr at 37° C., radioactivity in supernatants was determined. Mean±SEM of 4 mice per group. Spleen cells from IL-12 gene-treated mice generated 3–4-fold higher levels of CTL activity than spleen cells from naive mice ($p<0.005$). These results indicate that IL-12 gene therapy generates systemic anti-tumor immunity.

In a similar study, using spleen cells from mice that had previously rejected L5178Y tumors, CTL generated were able to lyse L5178Y cells but not syngeneic P815 cells.

All in all, the results indicate that IL-12 gene therapy with a particle-mediated gene transfer instrument is effective against various murine tumors and may be applied as a treatment of immunogenic human tumors. In addition, the findings indicate that IL-12 DNA is delivered into skin, but not into the tumor tissue following in vivo bombardment. Therefore, particle-mediated IL-12 gene therapy can be routinely applied to subcutaneous tumors or metastatic nodules without any surgical manipulations.

Furthermore, the inventors found about 250 pg of IL-12 at the tumor bombardment site which is about 1/400 to 1/40,000 of the "therapeutic dose" of recombinant IL-12 (0.1–10 µg). Moreover, the therapeutic dose of IL-12 is also known to cause unacceptable toxicity levels. Therefore, in comparison with treatment with recombinant IL-12, treatment with the IL-12 gene therapy of the present invention is much less (if at all) toxic, and much less expensive.

Thus it is demonstrated that circulating levels of cytokine IL-12 can be created in vivo by delivering into a patient in need of treatment for a tumor not quantities of IL-12 itself, but rather by delivering into the patient gene sequences causing expression of IL-12 in cells in the treated individual. The gene therapy method of the present invention enables the creation of an anti-tumor response in a treated individual without delivering IL-12 protein into the individual.

We claim:

1. A method of treating tumors in a mammal, comprising:
   a) providing a vector comprising an expressible genetic construct, wherein said genetic construct comprises a first DNA sequence encoding a p35 subunit of IL-12 and a second DNA sequence encoding a p40 subunit of IL-12, wherein said first and second DNA sequences are operably linked to a promoter; and
   b) introducing the vector into a target cell of the mammal in vivo, wherein said vector is delivered into tissue surrounding or adjacent to a tumor, and whereby said first and second DNA sequences are expressed by the cell to provide said IL-12 subunits at a level sufficient to inhibit tumor growth.

2. The method of claim 1, wherein the p35 DNA sequence encodes the peptide of SEQ ID NO:2 and the p40 DNA sequence encodes the peptide of SEQ ID NO:3.

3. The method of claim 1, wherein the DNA sequence encoding the p35 subunit is SEQ ID NO:1 at bases 953–1258 and 1332–1673 and the DNA sequence encoding the p40 subunit is SEQ ID NO:1 at bases 2377–3381.

4. The method of claim 1 wherein the target cell is an epidermal cell.

5. The method of claim 1, wherein the vector further comprises an internal ribosome entry site element between the first and second DNA sequences.

6. A method as claimed in claim 1 wherein the genetic construct is pWRG3169.

7. A method as claimed in claim 1 wherein the genetic construct is pWRG3196.

8. The method of claim 1 wherein the delivering step comprises the steps of:
   coating the copies of the vector onto carrier particles small in size in relation to the size of the cells of the mammal; and
   accelerating the coated carrier particles into target cells of the mammal in vivo.

9. The method of claim 8, wherein the carrier particles are accelerated by a gaseous discharge.

10. A vector comprising:
a) a first nucleic acid sequence encoding a p35 subunit of IL-12 operatively linked to a first promoter;
b) a second nucleic acid sequence encoding a p40 subunit of IL-12 operatively linked to a second promoter.

11. The vector of claim 10, wherein the vector is a plasmid.

12. The vector of claim 10, wherein the first and second promoters are cytomegalovirus (CMV) promoters.

13. The vector of claim 10, further comprising a first splicing donor/acceptor site between said first nucleic acid sequence and said first promoter, and a second splicing donor/acceptor site between said second nucleic acid sequence and said second promoter.

14. The vector of claim 13, wherein the splicing donor/acceptor is an SV40 splicing donor/acceptor.

15. A method of treating tumors in a mammal, comprising:
a) providing a vector of claim 10; and
b) introducing the vector into a target cell of the mammal in vivo, wherein said vector is delivered into tissue surrounding or adjacent to a tumor, and whereby said first and second DNA sequences are expressed by the cell to provide said IL-12 subunits at a level sufficient to inhibit tumor growth.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 7287 base pairs
      (B) TYPE: nucleic acid
      (C) STRANDEDNESS: double
      (D) TOPOLOGY: circular (ii) MOLECULE TYPE: other nucleic acid
      (A) DESCRIPTION: /desc = "Plasmid DNA"

(vii) IMMEDIATE SOURCE:
      (B) CLONE: pWRG3169

(ix) FEATURE:
      (A) NAME/KEY: promoter
      (B) LOCATION: 1..628

(ix) FEATURE:
      (A) NAME/KEY: iDNA
      (B) LOCATION: 629..810

(ix) FEATURE:
      (A) NAME/KEY: CDS
      (B) LOCATION: join(953..1258, 1332..1673)
      (D) OTHER INFORMATION: /product= "p35 gene product"

(ix) FEATURE:
      (A) NAME/KEY: polyA_site
      (B) LOCATION: 1797..2024

(ix) FEATURE:
      (A) NAME/KEY: promoter
      (B) LOCATION: 2110..2737

(ix) FEATURE:
    (A) NAME/KEY: iDNA
    (B) LOCATION: 2738..2919

(ix) FEATURE:
    (A) NAME/KEY: CDS
    (B) LOCATION: 2983..3990
    (D) OTHER INFORMATION: /product= "p40 gene product"

(ix) FEATURE:
    (A) NAME/KEY: polyA_site
    (B) LOCATION: 4075..4306

(xi) SEQUENCE DESCRIPTION: SEQ ID NO:1:

```
CGTTACATAA CTTACGGTAA ATGGCCCGCC TGGCTGACCG CCCAACGACC CCCGCCCATT     60

GACGTCAATA ATGACGTATG TTCCCATAGT AACGCCAATA GGGACTTTCC ATTGACGTCA    120

ATGGGTGGAG TATTTACGGT AAACTGCCCA CTTGGCAGTA CATCAAGTGT ATCATATGCC    180

AAGTACGCCC CCTATTGACG TCAATGACGG TAAATGGCCC GCCTGGCATT ATGCCCAGTA    240

CATGACCTTA TGGGACTTTC CTACTTGGCA GTACATCTAC GTATTAGTCA TCGCTATTAC    300

CATGGTGATG CGGTTTTGGC AGTACATCAA TGGGCGTGGA TAGCGGTTTG ACTCACGGGG    360

ATTTCCAAGT CTCCACCCCA TTGACGTCAA TGGGAGTTTG TTTTGGCACC AAAATCAACG    420

GGACTTTCCA AAATGTCGTA ACAACTCCGC CCCATTGACG CAAATGGGCG GTAGGCGTGT    480

ACGGTGGGAG GTCTATATAA GCAGAGCTCG TTTAGTGAAC CGTCAGATCG CCTGGAGACG    540

CCATCCACGC TGTTTTGACC TCCATAGAAG ACACCGGGAC CGATCCAGCC TCCGCGGCCG    600

GGAACGGTGC ATTGGAACGG ACTCTAGACT CCAGGAACTG AAAAACCAGA AAGTTAACTG    660

GTAAGTTTAG TCTTTTTGTC TTTTATTTCA GGTCCCGGAT CCGGTGGTGG TGCAAATCAA    720

AGAACTGCTC CTCAGTGGAT GTTGCCTTTA CTTCTAGGCC TGTACGGAAG TGTTACTTCT    780

GCTCTAAAAG CTGCGGAATT GTACCCGCGG CCGCAGCTTG GAATTCGATA ATTCGGCTTT    840

CCTGGGAAAG TCTGCCGGCT ATCCAGACAA TTATAAAAAT GTGTCTCCCA AGGTCAGCGT    900

TCCAACAGCC TCACCCTCGG CATCCAGCAG CTCCTCTCAG TGCCGGTCCA GC ATG        955
                                                         Met
                                                          1

TGT CAA TCA CGC TAC CTC CTC TTT TTG GCC ACC CTT GCC CTC CTA AAC    1003
Cys Gln Ser Arg Tyr Leu Leu Phe Leu Ala Thr Leu Ala Leu Leu Asn
          5                  10                  15

CAC CTC AGT TTG GCC AGG GTC ATT CCA GTC TCT GGA CCT GCC AGG TGT    1051
His Leu Ser Leu Ala Arg Val Ile Pro Val Ser Gly Pro Ala Arg Cys
         20                  25                  30

CTT AGC CAG TCC CGA AAC CTG CTG AAG ACC ACA GAT GAC ATG GTG AAG    1099
Leu Ser Gln Ser Arg Asn Leu Leu Lys Thr Thr Asp Asp Met Val Lys
     35                  40                  45

ACG GCC AGA GAA AAA CTG AAA CAT TAT TCC TGC ACT GCT GAA GAC ATC    1147
Thr Ala Arg Glu Lys Leu Lys His Tyr Ser Cys Thr Ala Glu Asp Ile
 50                  55                  60                  65

GAT CAT GAA GAC ATC ACA CGG GAC CAA ACC AGC ACA TTG AAG ACC TGT    1195
Asp His Glu Asp Ile Thr Arg Asp Gln Thr Ser Thr Leu Lys Thr Cys
                 70                  75                  80

TTA CCA CTG GAA CTA CAC AAG AAC GAG AGT TGC CTG GCT ACT AGA GAG    1243
Leu Pro Leu Glu Leu His Lys Asn Glu Ser Cys Leu Ala Thr Arg Glu
             85                  90                  95

ACT TCT TCC ACA ACA GTAAGTAAGC ACTCTAAGGG TTCCTTCCCC ATGACGGATT    1298
Thr Ser Ser Thr Thr
            100

CATAACACTG ATGCCTGGTC ATTCTTTCTC TAG AGA GGG AGC TGC CTG CCC CCA    1352
                                   Arg Gly Ser Cys Leu Pro Pro
                                                       105
```

```
CAG AAG ACG TCT TTG ATG ATG ACC CTG TGC CTT GGT AGC ATC TAT GAG    1400
Gln Lys Thr Ser Leu Met Met Thr Leu Cys Leu Gly Ser Ile Tyr Glu
110             115                 120                 125

GAC TTG AAG ATG TAC CAG ACA GAG TTC CAG GCC ATC AAC GCA GCA CTT    1448
Asp Leu Lys Met Tyr Gln Thr Glu Phe Gln Ala Ile Asn Ala Ala Leu
                130                 135                 140

CAG AAT CAC AAC CAT CAG CAG ATC ATT CTA GAC AAG GGC ATG CTG GTG    1496
Gln Asn His Asn His Gln Gln Ile Ile Leu Asp Lys Gly Met Leu Val
            145                 150                 155

GCC ATC GAT GAG CTG ATG CAG TCT CTG AAT CAT AAT GGC GAG ACT CTG    1544
Ala Ile Asp Glu Leu Met Gln Ser Leu Asn His Asn Gly Glu Thr Leu
        160                 165                 170

CGC CAG AAA CCT CCT GTG GGA GAA GCA GAC CCT TAC AGA GTG AAA ATG    1592
Arg Gln Lys Pro Pro Val Gly Glu Ala Asp Pro Tyr Arg Val Lys Met
    175                 180                 185

AAG CTC TGC ATC CTG CTT CAC GCC TTC AGC ACC CGC GTC GTG ACC ATC    1640
Lys Leu Cys Ile Leu Leu His Ala Phe Ser Thr Arg Val Val Thr Ile
190                 195                 200                 205

AAC AGG GTG ATG GGC TAT CTG AGC TCC GCC TGA AAGGCTCAAG GCCCTCTGCC  1693
Asn Arg Val Met Gly Tyr Leu Ser Ser Ala  *
                210                 215

ACAGCGCCCT CCTCACACAG ATAGGAAAAG CCGAATTATC AAGCTTATCG ATACCGTCGA  1753

CCTCGAGGGG GGGCCCTATT CTATAGTGTC ACCTAAATGC TAGAGCTCGC TGATCAGCCT  1813

CGACTGTGCC TTCTAGTTGC CAGCCATCTG TTGTTTGCCC CTCCCCCGTG CCTTCCTTGA  1873

CCCTGGAAGG TGCCACTCCC ACTGTCCTTT CCTAATAAAA TGAGGAAATT GCATCGCATT  1933

GTCTGAGTAG GTGTCATTCT ATTCTGGGGG GTGGGGTGGG GCAGGACAGC AAGGGGGAGG  1993

ATTGGGAAGA CAATAGCAGG CATGCTGGGG ATGCGGTGGG CTCTATGGAA CCAGCTGGGG  2053

CTCGAGGGGG GGCCCGGTAC GGGCTGCAGG AATTCGAGCT TGCATGCCTG CAGGTCCGTT  2113

ACATAACTTA CGGTAAATGG CCCGCCTGGC TGACCGCCCA ACGACCCCCG CCCATTGACG  2173

TCAATAATGA CGTATGTTCC CATAGTAACG CCAATAGGGA CTTTCCATTG ACGTCAATGG  2233

GTGGAGTATT TACGGTAAAC TGCCCACTTG CAGTACATCA AGTGTATCA TATGCCAAGT   2293

ACGCCCCCTA TTGACGTCAA TGACGGTAAA TGGCCCGCCT GGCATTATGC CCAGTACATG  2353

ACCTTATGGG ACTTTCCTAC TTGGCAGTAC ATCTACGTAT TAGTCATCGC TATTACCATG  2413

GTGATGCGGT TTTGGCAGTA CATCAATGGG CGTGGATAGC GGTTTGACTC ACGGGGATTT  2473

CCAAGTCTCC ACCCCATTGA CGTCAATGGG AGTTTGTTTT GGCACCAAAA TCAACGGGAC  2533

TTTCCAAAAT GTCGTAACAA CTCCGCCCCA TTGACGCAAA TGGGCGGTAG CGTGTACGG   2593

TGGGAGGTCT ATATAAGCAG AGCTCGTTTA GTGAACCGTC AGATCGCCTG GAGACGCCAT  2653

CCACGCTGTT TTGACCTCCA TAGAAGACAC CGGGACCGAT CCAGCCTCCG CGGCCGGGAA  2713

CGGTGCATTG GAACGGACTC TAGACTCCAG GAACTGAAAA ACCAGAAAGT TAACTGGTAA  2773

GTTTAGTCTT TTTGTCTTTT ATTTCAGGTC CCGGATCCGG TGGTGGTGCA AATCAAAGAA  2833

CTGCTCCTCA GTGGATGTTG CCTTTACTTC TAGGCCTGTA CGGAAGTGTT ACTTCTGCTC  2893

TAAAAGCTGC GGAATTGTAC CCGCGGCCGC AGCTTGGAAT TCGATAATTC GGCTTGCACA  2953

TCAGACCAGG CAGCTCGCAG CAAAGCAAG ATG TGT CCT CAG AAG CTA ACC ATC    3006
                                Met Cys Pro Gln Lys Leu Thr Ile
                                 1               5

TCC TGG TTT GCC ATC GTT TTG CTG GTG TCT CCA CTC ATG GCC ATG TGG   3054
Ser Trp Phe Ala Ile Val Leu Leu Val Ser Pro Leu Met Ala Met Trp
        10                  15                  20
```

-continued

| | |
|---|---|
| GAG CTG GAG AAA GAC GTT TAT GTT GTA GAG GTG GAC TGG ACT CCC GAT<br>Glu Leu Glu Lys Asp Val Tyr Val Val Glu Val Asp Trp Thr Pro Asp<br>25                            30                            35                            40 | 3102 |
| GCC CCT GGA GAA ACA GTG AAC CTC ACC TGT GAC ACG CCT GAA GAA GAT<br>Ala Pro Gly Glu Thr Val Asn Leu Thr Cys Asp Thr Pro Glu Glu Asp<br>                      45                            50                            55 | 3150 |
| GAC ATC ACC TGG ACC TCA GAC CAG AGA CAT GGA GTC ATA GGC TCT GGA<br>Asp Ile Thr Trp Thr Ser Asp Gln Arg His Gly Val Ile Gly Ser Gly<br>                  60                            65                            70 | 3198 |
| AAG ACC CTG ACC ATC ACT GTC AAA GAG TTT CTA GAT GCT GGC CAG TAC<br>Lys Thr Leu Thr Ile Thr Val Lys Glu Phe Leu Asp Ala Gly Gln Tyr<br>75                            80                            85 | 3246 |
| ACC TGC CAC AAA GGA GGC GAG ACT CTG AGC CAC TCA CAT CTG CTG CTC<br>Thr Cys His Lys Gly Gly Glu Thr Leu Ser His Ser His Leu Leu Leu<br>      90                            95                            100 | 3294 |
| CAC AAG AAG GAA AAT GGA ATT TGG TCC ACT GAA ATT TTA AAA AAT TTC<br>His Lys Lys Glu Asn Gly Ile Trp Ser Thr Glu Ile Leu Lys Asn Phe<br>105                       110                       115                      120 | 3342 |
| AAA AAC AAG ACT TTC CTG AAG TGT GAA GCA CCA AAT TAC TCC GGA CGG<br>Lys Asn Lys Thr Phe Leu Lys Cys Glu Ala Pro Asn Tyr Ser Gly Arg<br>                  125                       130                      135 | 3390 |
| TTC ACG TGC TCA TGG CTG GTG CAA AGA AAC ATG GAC TTG AAG TTC AAC<br>Phe Thr Cys Ser Trp Leu Val Gln Arg Asn Met Asp Leu Lys Phe Asn<br>         140                       145                       150 | 3438 |
| ATC AAG AGC AGT AGC AGT TCC CCT GAC TCT CGG GCA GTG ACA TGT GGA<br>Ile Lys Ser Ser Ser Ser Pro Asp Ser Arg Ala Val Thr Cys Gly<br>              155                       160                       165 | 3486 |
| ATG GCG TCT CTG TCT GCA GAG AAG GTC ACA CTG GAC CAA AGG GAC TAT<br>Met Ala Ser Leu Ser Ala Glu Lys Val Thr Leu Asp Gln Arg Asp Tyr<br>170                       175                       180 | 3534 |
| GAG AAG TAT TCA GTG TCC TGC CAG GAG GAT GTC ACC TGC CCA ACT GCC<br>Glu Lys Tyr Ser Val Ser Cys Gln Glu Asp Val Thr Cys Pro Thr Ala<br>185                       190                       195                      200 | 3582 |
| GAG GAG ACC CTG CCC ATT GAA CTG GCG TTG GAA GCA CGG CAG CAG AAT<br>Glu Glu Thr Leu Pro Ile Glu Leu Ala Leu Glu Ala Arg Gln Gln Asn<br>                  205                       210                      215 | 3630 |
| AAA TAT GAG AAC TAC AGC ACC AGC TTC TTC ATC AGG GAC ATC ATC AAA<br>Lys Tyr Glu Asn Tyr Ser Thr Ser Phe Phe Ile Arg Asp Ile Ile Lys<br>                  220                       225                      230 | 3678 |
| CCA GAC CCG CCC AAG AAC TTG CAG ATG AAG CCT TTG AAG AAC TCA CAG<br>Pro Asp Pro Pro Lys Asn Leu Gln Met Lys Pro Leu Lys Asn Ser Gln<br>             235                       240                       245 | 3726 |
| GTG GAG GTC AGC TGG GAG TAC CCT GAC TCC TGG AGC ACT CCC CAT TCC<br>Val Glu Val Ser Trp Glu Tyr Pro Asp Ser Trp Ser Thr Pro His Ser<br>250                       255                       260 | 3774 |
| TAC TTC TCC CTC AAG TTC TTT GTT CGA ATC CAG CGC AAG AAA GAA AAG<br>Tyr Phe Ser Leu Lys Phe Phe Val Arg Ile Gln Arg Lys Lys Glu Lys<br>265                       270                       275                      280 | 3822 |
| ATG AAG GAG ACA GAG GAG GGG TGT AAC CAG AAA GGT GCG TTC CTC GTA<br>Met Lys Glu Thr Glu Glu Gly Cys Asn Gln Lys Gly Ala Phe Leu Val<br>                  285                       290                      295 | 3870 |
| GAG AAG ACA TCT ACC GAA GTC CAA TGC AAA GGC GGG AAT GTC TGC GTG<br>Glu Lys Thr Ser Thr Glu Val Gln Cys Lys Gly Gly Asn Val Cys Val<br>                      300                       305                      310 | 3918 |
| CAA GCT CAG GAT CGC TGT TAC AAT TCC TCG TGC AGC AAG TGG GCA TGT<br>Gln Ala Gln Asp Arg Cys Tyr Asn Ser Ser Cys Ser Lys Trp Ala Cys<br>315                       320                       325 | 3966 |
| GTT CCC TGC AGG GTC CGA TCC TAG GATGCAACGT TGAAGCCGAA TTATCAAGCT<br>Val Pro Cys Arg Val Arg Ser  *<br>330                       335 | 4020 |

```
TATCGATACC GTCGACCTCG AGGGGGGGCC CTATTCTATA GTGTCACCTA AATGCTAGAG    4080

CTCGCTGATC AGCCTCGACT GTGCCTTCTA GTTGCCAGCC ATCTGTTGTT TGCCCCTCCC    4140

CCGTGCCTTC CTTGACCCTG GAAGGTGCCA CTCCCACTGT CCTTTCCTAA TAAAATGAGG    4200

AAATTGCATC GCATTGTCTG AGTAGGTGTC ATTCTATTCT GGGGGGTGGG GTGGGCAGG     4260

ACAGCAAGGG GGAGGATTGG GAAGACAATA GCAGGCATGC TGGGGATGCG GTGGGCTCTA    4320

TGGAACCAGC TGGGGCTCGA GGGGGGGCCC GGTACCCAAT TCGCCCTATA GTGAGTCGTA    4380

TTACAATTCA CTGGCCGTCG TTTTACAACG TCGTGACTGG GAAAACCCTG GCGTTACCCA    4440

ACTTAATCGC CTTGCAGCAC ATCCCCCTTT CGCCAGCTGG CGTAATAGCG AAGAGGCCCG    4500

CACCGATCGC CCTTCCCAAC AGTTGCGCAG CCTGAATGGC GAATGGGACG CGCCCTGTAG    4560

CGGCGCATTA AGCGCGGCGG GTGTGGTGGT TACGCGCAGC GTGACCGCTA CACTTGCCAG    4620

CGCCCTAGCG CCCGCTCCTT TCGCTTTCTT CCCTTCCTTT CTCGCCACGT TCGCCGGCTT    4680

TCCCCGTCAA GCTCTAAATC GGGGGCTCCC TTTAGGGTTC CGATTTAGTG CTTTACGGCA    4740

CCTCGACCCC AAAAAACTTG ATTAGGGTGA TGGTTCACGT AGTGGGCCAT CGCCCTGATA    4800

GACGGTTTTT CGCCCTTTGA CGTTGGAGTC CACGTTCTTT AATAGTGGAC TCTTGTTCCA    4860

AACTGGAACA ACACTCAACC CTATCTCGGT CTATTCTTTT GATTTATAAG GGATTTTGCC    4920

GATTTCGGCC TATTGGTTAA AAAATGAGCT GATTTAACAA AAATTTAACG CGAATTTTAA    4980

CAAAATATTA ACGCTTACAA TTTAGGTGGC ACTTTTCGGG GAAATGTGCG CGGAACCCCT    5040

ATTTGTTTAT TTTTCTAAAT ACATTCAAAT ATGTATCCGC TCATGAGACA ATAACCCTGA    5100

TAAATGCTTC AATAATATTG AAAAAGGAAG AGTATGAGTA TTCAACATTT CCGTGTCGCC    5160

CTTATTCCCT TTTTTGCGGC ATTTTGCCTT CCTGTTTTTG CTCACCCAGA AACGCTGGTG    5220

AAAGTAAAAG ATGCTGAAGA TCAGTTGGGT GCACGAGTGG GTTACATCGA ACTGGATCTC    5280

AACAGCGGTA AGATCCTTGA GAGTTTTCGC CCCGAAGAAC GTTTTCCAAT GATGAGCACT    5340

TTTAAAGTTC TGCTATGTGG CGCGGTATTA TCCCGTATTG ACGCCGGGCA AGAGCAACTC    5400

GGTCGCCGCA TACACTATTC TCAGAATGAC TTGGTTGAGT ACTCACCAGT CACAGAAAAG    5460

CATCTTACGG ATGGCATGAC AGTAAGAGAA TTATGCAGTG CTGCCATAAC CATGAGTGAT    5520

AACACTGCGG CCAACTTACT TCTGACAACG ATCGGAGGAC CGAAGGAGCT AACCGCTTTT    5580

TTGCACAACA TGGGGGATCA TGTAACTCGC CTTGATCGTT GGGAACCGGA GCTGAATGAA    5640

GCCATACCAA ACGACGAGCG TGACACCACG ATGCCTGTAG CAATGGCAAC AACGTTGCGC    5700

AAACTATTAA CTGGCGAACT ACTTACTCTA GCTTCCCGGC AACAATTAAT AGACTGGATG    5760

GAGGCGGATA AAGTTGCAGG ACCACTTCTG CGCTCGGCCC TTCCGGCTGG CTGGTTTATT    5820

GCTGATAAAT CTGGAGCCGG TGAGCGTGGG TCTCGCGGTA TCATTGCAGC ACTGGGGCCA    5880

GATGGTAAGC CCTCCCGTAT CGTAGTTATC TACACGACGG GGAGTCAGGC AACTATGGAT    5940

GAACGAAATA GACAGATCGC TGAGATAGGT GCCTCACTGA TTAAGCATTG GTAACTGTCA    6000

GACCAAGTTT ACTCATATAT ACTTTAGATT GATTTAAAAC TTCATTTTTA ATTTAAAAGG    6060

ATCTAGGTGA AGATCCTTTT TGATAATCTC ATGACCAAAA TCCCTTAACG TGAGTTTTCG    6120

TTCCACTGAG CGTCAGACCC CGTAGAAAAG ATCAAAGGAT CTTCTTGAGA TCCTTTTTTT    6180

CTGCGCGTAA TCTGCTGCTT GCAAACAAAA AAACCACCGC TACCAGCGGT GGTTTGTTTG    6240

CCGGATCAAG AGCTACCAAC TCTTTTTCCG AAGGTAACTG GCTTCAGCAG AGCGCAGATA    6300

CCAAATACTG TCCTTCTAGT GTAGCCGTAG TTAGGCCACC ACTTCAAGAA CTCTGTAGCA    6360

CCGCCTACAT ACCTCGCTCT GCTAATCCTG TTACCAGTGG CTGCTGCCAG TGGCGATAAG    6420
```

-continued

```
TCGTGTCTTA CCGGGTTGGA CTCAAGACGA TAGTTACCGG ATAAGGCGCA GCGGTCGGGC    6480

TGAACGGGGG GTTCGTGCAC ACAGCCCAGC TTGGAGCGAA CGACCTACAC CGAACTGAGA    6540

TACCTACAGC GTGAGCTATG AGAAAGCGCC ACGCTTCCCG AAGGGAGAAA GGCGGACAGG    6600

TATCCGGTAA GCGGCAGGGT CGGAACAGGA GAGCGCACGA GGGAGCTTCC AGGGGGAAAC    6660

GCCTGGTATC TTTATAGTCC TGTCGGGTTT CGCCACCTCT GACTTGAGCG TCGATTTTTG    6720

TGATGCTCGT CAGGGGGGCG GAGCCTATGG AAAAACGCCA GCAACGCGGC CTTTTTACGG    6780

TTCCTGGCCT TTTGCTGGCC TTTTGCTCAC ATGTTCTTTC CTGCGTTATC CCCTGATTCT    6840

GTGGATAACC GTATTACCGC CTTTGAGTGA GCTGATACCG CTCGCCGCAG CCGAACGACC    6900

GAGCGCAGCG AGTCAGTGAG CGAGGAAGCG AAGAGCGCC CAATACGCAA ACCGCCTCTC     6960

CCCGCGCGTT GGCCGATTCA TTAATGCAGC TGGCACGACA GGTTTCCCGA CTGGAAAGCG    7020

GGCAGTGAGC GCAACGCAAT TAATGTGAGT TAGCTCACTC ATTAGGCACC CCAGGCTTTA    7080

CACTTTATGC TTCCGGCTCG TATGTTGTGT GGAATTGTGA GCGGATAACA ATTTCACACA    7140

GGAAACAGCT ATGACCATGA TTACGCCAAG CTCGAAATTA ACCCTCACTA AAGGGAACAA    7200

AAGCTGGAGC TCCACCGCGG TGGCGGCCGC TCTAGAACTA GTGGATCCCC CGGGCTGCAG    7260

GAATTCGAGC TTGCATGCCT GCAGGTC                                       7287
```

(2) INFORMATION FOR SEQ ID NO:2:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO:2:

```
Met Cys Gln Ser Arg Tyr Leu Leu Phe Leu Ala Thr Leu Ala Leu Leu
  1               5                  10                  15

Asn His Leu Ser Leu Ala Arg Val Ile Pro Val Ser Gly Pro Ala Arg
                 20                  25                  30

Cys Leu Ser Gln Ser Arg Asn Leu Leu Lys Thr Thr Asp Asp Met Val
             35                  40                  45

Lys Thr Ala Arg Glu Lys Leu Lys His Tyr Ser Cys Thr Ala Glu Asp
 50                  55                  60

Ile Asp His Glu Asp Ile Thr Arg Asp Gln Thr Ser Thr Leu Lys Thr
 65                  70                  75                  80

Cys Leu Pro Leu Glu Leu His Lys Asn Glu Ser Cys Leu Ala Thr Arg
                 85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
            115                 120                 125

Met Tyr Gln Thr Glu Phe Gln Ala Ile Asn Ala Ala Leu Gln Asn His
130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
            195                 200                 205
```

```
Met Gly Tyr Leu Ser Ser Ala
    210             215
```

(2) INFORMATION FOR SEQ ID NO:3:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO:3:

```
Met Cys Pro Gln Lys Leu Thr Ile Ser Trp Phe Ala Ile Val Leu Leu
 1               5                  10                  15

Val Ser Pro Leu Met Ala Met Trp Glu Leu Glu Lys Asp Val Tyr Val
                20                  25                  30

Val Glu Val Asp Trp Thr Pro Asp Ala Pro Gly Glu Thr Val Asn Leu
            35                  40                  45

Thr Cys Asp Thr Pro Glu Glu Asp Asp Ile Thr Trp Thr Ser Asp Gln
        50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Cys Tyr Asn
305                 310                 315                 320

Ser Ser Cys Ser Lys Trp Ala Cys Val Pro Cys Arg Val Arg Ser
                325                 330                 335
```

(2) INFORMATION FOR SEQ ID NO:4:

(i) SEQUENCE CHARACTERISTICS:
        (A) LENGTH: 6295 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "plasmid pWRG3196"

(ix) FEATURE:
        (A) NAME/KEY: CDS
        (B) LOCATION: join(955..1260, 1334..1675)
        (D) OTHER INFORMATION: /product= "p35 gene product"

(ix) FEATURE:
        (A) NAME/KEY: CDS
        (B) LOCATION: 2377..3384
        (D) OTHER INFORMATION: /product= "p40 gene product"

(xi) SEQUENCE DESCRIPTION: SEQ ID NO:4:

```
GAATTCGAGC TTGCATGCCT GCAGGTCGTT ACATAACTTA CGGTAAATGG CCCGCCTGGC      60

TGACCGCCCA ACGACCCCCG CCCATTGACG TCAATAATGA CGTATGTTCC CATAGTAACG     120

CCAATAGGGA CTTTCCATTG ACGTCAATGG GTGGAGTATT TACGGTAAAC TGCCCACTTG     180

GCAGTACATC AAGTGTATCA TATGCCAAGT ACGCCCCCTA TTGACGTCAA TGACGGTAAA     240

TGGCCCGCCT GGCATTATGC CCAGTACATG ACCTTATGGG ACTTTCCTAC TTGGCAGTAC     300

ATCTACGTAT TAGTCATCGC TATTACCATG GTGATGCGGT TTTGGCAGTA CATCAATGGG     360

CGTGGATAGC GGTTTGACTC ACGGGGATTT CCAAGTCTCC ACCCCATTGA CGTCAATGGG     420

AGTTTGTTTT GGCACCAAAA TCAACGGGAC TTTCCAAAAT GTCGTAACAA CTCCGCCCCA     480

TTGACGCAAA TGGGCGGTAG GCGTGTACGG TGGGAGGTCT ATATAAGCAG AGCTCGTTTA     540

GTGAACCGTC AGATCGCCTG AGACGCCCAT CCACGCTGTT TTGACCTCCA TAGAAGACAC     600

CGGGACCGAT CCAGCCTCCG GACTCTAGAG GATCCGGTAC TCGAGGAACT GAAAAACCAG     660

AAAGTTAACT GGTAAGTTTA GTCTTTTTGT CTTTTATTTC AGGTCCCGGA TCCGGTGGTG     720

GTGCAAATCA AGAACTGCT CCTCAGTGGA TGTTGCCTTT ACTTCTAGGC CTGTACGGAA     780

GTGTTACTTC TGCTCTAAAA GCTGCGGAAT TGTACCCGCG GCCGGTGGTT AAATTCGGCT     840

TTCCTGGGAA AGTCTGCCGG CTATCCAGAC AATTATAAAA ATGTGTCTCC CAAGGTCAGC     900

GTTCCAACAG CCTCACCCTC GGCATCCAGC AGCTCCTCTC AGTGCCGGTC CAGC ATG      957
                                                              Met
                                                                1

TGT CAA TCA CGC TAC CTC CTC TTT TTG GCC ACC CTT GCC CTC CTA AAC   1005
Cys Gln Ser Arg Tyr Leu Leu Phe Leu Ala Thr Leu Ala Leu Leu Asn
          5                  10                  15

CAC CTC AGT TTG GCC AGG GTC ATT CCA GTC TCT GGA CCT GCC AGG TGT   1053
His Leu Ser Leu Ala Arg Val Ile Pro Val Ser Gly Pro Ala Arg Cys
         20                  25                  30

CTT AGC CAG TCC CGA AAC CTG CTG AAG ACC ACA GAT GAC ATG GTG AAG   1101
Leu Ser Gln Ser Arg Asn Leu Leu Lys Thr Thr Asp Asp Met Val Lys
     35                  40                  45

ACG GCC AGA GAA AAA CTG AAA CAT TAT TCC TGC ACT GCT GAA GAC ATC   1149
Thr Ala Arg Glu Lys Leu Lys His Tyr Ser Cys Thr Ala Glu Asp Ile
 50                  55                  60                  65

GAT CAT GAA GAC ATC ACA CGG GAC CAA ACC AGC ACA TTG AAG ACC TGT   1197
Asp His Glu Asp Ile Thr Arg Asp Gln Thr Ser Thr Leu Lys Thr Cys
                 70                  75                  80

TTA CCA CTG GAA CTA CAC AAG AAC GAG AGT TGC CTG GCT ACT AGA GAG   1245
Leu Pro Leu Glu Leu His Lys Asn Glu Ser Cys Leu Ala Thr Arg Glu
             85                  90                  95
```

```
ACT TCT TCC ACA ACA GTAAGTAAGC ACTCTAAGGG TTCCTTCCCC ATGACGGATT      1300
Thr Ser Ser Thr Thr
            100

CATAACACTG ATGCCTGGTC ATTCTTTCTC TAG AGA GGG AGC TGC CTG CCC CCA     1354
                                    Arg Gly Ser Cys Leu Pro Pro
                                                105

CAG AAG ACG TCT TTG ATG ATG ACC CTG TGC CTT GGT AGC ATC TAT GAG      1402
Gln Lys Thr Ser Leu Met Met Thr Leu Cys Leu Gly Ser Ile Tyr Glu
110             115                 120                 125

GAC TTG AAG ATG TAC CAG ACA GAG TTC CAG GCC ATC AAC GCA GCA CTT      1450
Asp Leu Lys Met Tyr Gln Thr Glu Phe Gln Ala Ile Asn Ala Ala Leu
                130                 135                 140

CAG AAT CAC AAC CAT CAG CAG ATC ATT CTA GAC AAG GGC ATG CTG GTG      1498
Gln Asn His Asn His Gln Gln Ile Ile Leu Asp Lys Gly Met Leu Val
            145                 150                 155

GCC ATC GAT GAG CTG ATG CAG TCT CTG AAT CAT AAT GGC GAG ACT CTG      1546
Ala Ile Asp Glu Leu Met Gln Ser Leu Asn His Asn Gly Glu Thr Leu
        160                 165                 170

CGC CAG AAA CCT CCT GTG GGA GAA GCA GAC CCT TAC AGA GTG AAA ATG      1594
Arg Gln Lys Pro Pro Val Gly Glu Ala Asp Pro Tyr Arg Val Lys Met
    175                 180                 185

AAG CTC TGC ATC CTG CTT CAC GCC TTC AGC ACC CGC GTC GTG ACC ATC      1642
Lys Leu Cys Ile Leu Leu His Ala Phe Ser Thr Arg Val Val Thr Ile
190             195                 200                 205

AAC AGG GTG ATG GGC TAT CTG AGC TCC GCC TGA AAGGCTCAAG GCCCTCTGCC    1695
Asn Arg Val Met Gly Tyr Leu Ser Ser Ala *
                210                 215

ACAGCGCCCT CCTCACACAG ATAGGAAAAG CCGAATTTAA GATATCACTA GTGAATTCCG    1755

CCCCTCTCCC TCCCCCCCCC CTAACGTTAC TGGCCGAAGC CGCTTGGAAT AAGGCCGGTG    1815

TGCGTTTGTC TATATGTTAT TTTCCACCAT ATTGCCGTCT TTTGGCAATG TGAGGGCCCG    1875

GAAACCTGGC CCTGTCTTCT TGACGAGCAT TCCTAGGGGT CTTTCCCCTC TCGCCAAAGG    1935

AATGCAAGGT CTGTTGAATG TCGTGAAGGA AGCAGTTCCT CTGGAAGCTT CTTGAAGACA    1995

AACAACGTCT GTAGCGACCC TTTGCAGGCA GCGGAACCCC CCACCTGGCG ACAGGTGCCT    2055

CTGCGGCCAA AAGCCACGTG TATAAGATAC ACCTGCAAAG GCGGCACAAC CCCAGTGCCA    2115

CGTTGTGAGT TGGATAGTTG TGGAAAGAGT CAAATGGCTC TCCTCAAGCG TATTCAACAA    2175

GGGGCTGAAG GATGCCCAGA AGGTACCCCA TTGTATGGGA TCTGATCTGG GGCCTCGGTG    2235

CACATGCTTT ACATGTGTTT AGTCGAGGTT AAAAAACGTC TAGGCCCCCC GAACCACGGG    2295

GACGTGGTTT TCCTTTGAAA AACACGATGA TAATCCCAAT TCGGCTTGCA CATCAGACCA    2355

GGCAGCTCGC AGCAAAGCAA G ATG TGT CCT CAG AAG CTA ACC ATC TCC TGG      2406
                       Met Cys Pro Gln Lys Leu Thr Ile Ser Trp
                         1               5                  10

TTT GCC ATC GTT TTG CTG GTG TCT CCA CTC ATG GCC ATG TGG GAG CTG      2454
Phe Ala Ile Val Leu Leu Val Ser Pro Leu Met Ala Met Trp Glu Leu
                15                  20                  25

GAG AAA GAC GTT TAT GTT GTA GAG GTG GAC TGG ACT CCC GAT GCC CCT      2502
Glu Lys Asp Val Tyr Val Val Glu Val Asp Trp Thr Pro Asp Ala Pro
                30                  35                  40

GGA GAA ACA GTG AAC CTC ACC TGT GAC ACG CCT GAA GAA GAT GAC ATC      2550
Gly Glu Thr Val Asn Leu Thr Cys Asp Thr Pro Glu Glu Asp Asp Ile
            45                  50                  55

ACC TGG ACC TCA GAC CAG AGA CAT GGA GTC ATA GGC TCT GGA AAG ACC      2598
Thr Trp Thr Ser Asp Gln Arg His Gly Val Ile Gly Ser Gly Lys Thr
        60                  65                  70
```

```
CTG ACC ATC ACT GTC AAA GAG TTT CTA GAT GCT GGC CAG TAC ACC TGC    2646
Leu Thr Ile Thr Val Lys Glu Phe Leu Asp Ala Gly Gln Tyr Thr Cys
 75              80                  85                  90

CAC AAA GGA GGC GAG ACT CTG AGC CAC TCA CAT CTG CTG CTC CAC AAG    2694
His Lys Gly Gly Glu Thr Leu Ser His Ser His Leu Leu Leu His Lys
             95                 100                 105

AAG GAA AAT GGA ATT TGG TCC ACT GAA ATT TTA AAA AAT TTC AAA AAC    2742
Lys Glu Asn Gly Ile Trp Ser Thr Glu Ile Leu Lys Asn Phe Lys Asn
         110                 115                 120

AAG ACT TTC CTG AAG TGT GAA GCA CCA AAT TAC TCC GGA CGG TTC ACG    2790
Lys Thr Phe Leu Lys Cys Glu Ala Pro Asn Tyr Ser Gly Arg Phe Thr
             125                 130                 135

TGC TCA TGG CTG GTG CAA AGA AAC ATG GAC TTG AAG TTC AAC ATC AAG    2838
Cys Ser Trp Leu Val Gln Arg Asn Met Asp Leu Lys Phe Asn Ile Lys
140                 145                 150

AGC AGT AGC AGT TCC CCT GAC TCT CGG GCA GTG ACA TGT GGA ATG GCG    2886
Ser Ser Ser Ser Ser Pro Asp Ser Arg Ala Val Thr Cys Gly Met Ala
155                 160                 165                 170

TCT CTG TCT GCA GAG AAG GTC ACA CTG GAC CAA AGG GAC TAT GAG AAG    2934
Ser Leu Ser Ala Glu Lys Val Thr Leu Asp Gln Arg Asp Tyr Glu Lys
             175                 180                 185

TAT TCA GTG TCC TGC CAG GAG GAT GTC ACC TGC CCA ACT GCC GAG GAG    2982
Tyr Ser Val Ser Cys Gln Glu Asp Val Thr Cys Pro Thr Ala Glu Glu
         190                 195                 200

ACC CTG CCC ATT GAA CTG GCG TTG GAA GCA CGG CAG CAG AAT AAA TAT    3030
Thr Leu Pro Ile Glu Leu Ala Leu Glu Ala Arg Gln Gln Asn Lys Tyr
             205                 210                 215

GAG AAC TAC AGC ACC AGC TTC TTC ATC AGG GAC ATC ATC AAA CCA GAC    3078
Glu Asn Tyr Ser Thr Ser Phe Phe Ile Arg Asp Ile Ile Lys Pro Asp
        220                 225                 230

CCG CCC AAG AAC TTG CAG ATG AAG CCT TTG AAG AAC TCA CAG GTG GAG    3126
Pro Pro Lys Asn Leu Gln Met Lys Pro Leu Lys Asn Ser Gln Val Glu
235                 240                 245                 250

GTC AGC TGG GAG TAC CCT GAC TCC TGG AGC ACT CCC CAT TCC TAC TTC    3174
Val Ser Trp Glu Tyr Pro Asp Ser Trp Ser Thr Pro His Ser Tyr Phe
             255                 260                 265

TCC CTC AAG TTC TTT GTT CGA ATC CAG CGC AAG AAA GAA AAG ATG AAG    3222
Ser Leu Lys Phe Phe Val Arg Ile Gln Arg Lys Lys Glu Lys Met Lys
         270                 275                 280

GAG ACA GAG GAG GGG TGT AAC CAG AAA GGT GCG TTC CTC GTA GAG AAG    3270
Glu Thr Glu Glu Gly Cys Asn Gln Lys Gly Ala Phe Leu Val Glu Lys
             285                 290                 295

ACA TCT ACC GAA GTC CAA TGC AAA GGC GGG AAT GTC TGC GTG CAA GCT    3318
Thr Ser Thr Glu Val Gln Cys Lys Gly Gly Asn Val Cys Val Gln Ala
         300                 305                 310

CAG GAT CGC TGT TAC AAT TCC TCG TGC AGC AAG TGG GCA TGT GTT CCC    3366
Gln Asp Arg Cys Tyr Asn Ser Ser Cys Ser Lys Trp Ala Cys Val Pro
315                 320                 325                 330

TGC AGG GTC CGA TCC TAG GATGCAACGT TGAAGCCGAA TTGGGCGGCC           3414
Cys Arg Val Arg Ser  *
             335

GCATGCATCC CTCCGCGGGG ATCCAGACAT GATAAGATAC ATTGATGAGT TTGGACAAAC    3474

CACAACTAGA ATGCAGTGAA AAAAATGCTT TATTTGTGAA ATTTGTGATG CTATTGCTTT    3534

ATTTGTAACC ATTATAAGCT GCAATAAACA AGTTAACAAC AACAATTGCA TTCATTTTAT    3594

GTTTCAGGTT CAGGGGGAGG TGTGGGAGGT TTTTTCGGAT CCTCTAGAGT CGACCTGCAG    3654

GCATGCAAGC TTGGCGTAAT CATGGTCATA GCTGTTTCCT GTGTGAAATT GTTATCCGCT    3714

CACAATTCCA CACAACATAC GAGCCGGAAG CATAAAGTGT AAAGCCTGGG GTGCCTAATG    3774
```

```
AGTGAGCTAA CTCACATTAA TTGCGTTGCG CTCACTGCCC GCTTTCCAGT CGGGAAACCT    3834
GTCGTGCCAG CTGCATTAAT GAATCGGCCA ACGCGCGGGG AGAGGCGGTT TGCGTATTGG    3894
GCGCTCTTCC GCTTCCTCGC TCACTGACTC GCTGCGCTCG GTCGTTCGGC TGCGGCGAGC    3954
GGTATCAGCT CACTCAAAGG CGGTAATACG GTTATCCACA GAATCAGGGG ATAACGCAGG    4014
AAAGAACATG TGAGCAAAAG GCCAGCAAAA GGCCAGGAAC CGTAAAAAGG CCGCGTTGCT    4074
GGCGTTTTTC CATAGGCTCC GCCCCCCTGA CGAGCATCAC AAAAATCGAC GCTCAAGTCA    4134
GAGGTGGCGA AACCCGACAG GACTATAAAG ATACCAGGCG TTTCCCCCTG GAAGCTCCCT    4194
CGTGCGCTCT CCTGTTCCGA CCCTGCCGCT TACCGGATAC CTGTCCGCCT TTCTCCCTTC    4254
GGGAAGCGTG GCGCTTTCTC ATAGCTCACG CTGTAGGTAT CTCAGTTCGG TGTAGGTCGT    4314
TCGCTCCAAG CTGGGCTGTG TGCACGAACC CCCCGTTCAG CCCGACCGCT GCGCCTTATC    4374
CGGTAACTAT CGTCTTGAGT CCAACCCGGT AAGACACGAC TTATCGCCAC TGGCAGCAGC    4434
CACTGGTAAC AGGATTAGCA GAGCGAGGTA TGTAGGCGGT GCTACAGAGT TCTTGAAGTG    4494
GTGGCCTAAC TACGGCTACA CTAGAAGGAC AGTATTTGGT ATCTGCGCTC TGCTGAAGCC    4554
AGTTACCTTC GGAAAAAGAG TTGGTAGCTC TTGATCCGGC AAACAAACCA CCGCTGGTAG    4614
CGGTGGTTTT TTTGTTTGCA AGCAGCAGAT TACGCGCAGA AAAAAAGGAT CTCAAGAAGA    4674
TCCTTTGATC TTTTCTACGG GGTCTGACGC TCAGTGGAAC GAAAACTCAC GTTAAGGGAT    4734
TTTGGTCATG AGATTATCAA AAAGGATCTT CACCTAGATC CTTTTAAATT AAAAATGAAG    4794
TTTTAAATCA ATCTAAAGTA TATATGAGTA AACTTGGTCT GACAGTTACC AATGCTTAAT    4854
CAGTGAGGCA CCTATCTCAG CGATCTGTCT ATTTCGTTCA TCCATAGTTG CCTGACTCCC    4914
CGTCGTGTAG ATAACTACGA TACGGGAGGG CTTACCATCT GGCCCCAGTG CTGCAATGAT    4974
ACCGCGAGAC CCACGCTCAC CGGCTCCAGA TTTATCAGCA ATAAACCAGC CAGCCGGAAG    5034
GGCCGAGCGC AGAAGTGGTC CTGCAACTTT ATCCGCCTCC ATCCAGTCTA TTAATTGTTG    5094
CCGGGAAGCT AGAGTAAGTA GTTCGCCAGT TAATAGTTTG CGCAACGTTG TTGCCATTGC    5154
TACAGGCATC GTGGTGTCAC GCTCGTCGTT TGGTATGGCT TCATTCAGCT CCGGTTCCCA    5214
ACGATCAAGG CGAGTTACAT GATCCCCCAT GTTGTGCAAA AAAGCGGTTA GCTCCTTCGG    5274
TCCTCCGATC GTTGTCAGAA GTAAGTTGGC CGCAGTGTTA TCACTCATGG TTATGGCAGC    5334
ACTGCATAAT TCTCTTACTG TCATGCCATC CGTAAGATGC TTTTCTGTGA CTGGTGAGTA    5394
CTCAACCAAG TCATTCTGAG AATAGTGTAT GCGGCGACCG AGTTGCTCTT GCCCGGCGTC    5454
AATACGGGAT AATACCGCGC CACATAGCAG AACTTTAAAA GTGCTCATCA TTGGAAAACG    5514
TTCTTCGGGG CGAAAACTCT CAAGGATCTT ACCGCTGTTG AGATCCAGTT CGATGTAACC    5574
CACTCGTGCA CCCAACTGAT CTTCAGCATC TTTTACTTTC ACCAGCGTTT CTGGGTGAGC    5634
AAAAACAGGA AGGCAAAATG CCGCAAAAAA GGGAATAAGG GCGACACGGA AATGTTGAAT    5694
ACTCATACTC TTCCTTTTTC AATATTATTG AAGCATTTAT CAGGGTTATT GTCTCATGAG    5754
CGGATACATA TTTGAATGTA TTTAGAAAAA TAAACAAATA GGGGTTCCGC GCACATTTCC    5814
CCGAAAAGTG CCACCTGACG TCTAAGAAAC CATTATTATC ATGACATTAA CCTATAAAAA    5874
TAGGCGTATC ACGAGGCCCT TTCGTCTCGC GCGTTTCGGT GATGACGGTG AAAACCTCTG    5934
ACACATGCAG CTCCCGGAGA CGGTCACAGC TTGTCTGTAA GCGGATGCCG GGAGCAGACA    5994
AGCCCGTCAG GGCGCGTCAG CGGGTGTTGG CGGGTGTCGG GCTGGCTTA ACTATGCGGC     6054
ATCAGAGCAG ATTGTACTGA GAGTGCACCA TATGCGGTGT GAAATACCGC ACAGATGCGT    6114
AAGGAGAAAA TACCGCATCA GGCGCCATTC GCCATTCAGG CTGCGCAACT GTTGGGAAGG    6174
```

```
GCGATCGGTG CGGGCCTCTT CGCTATTACG CCAGCTGGCG AAAGGGGGAT GTGCTGCAAG      6234

GCGATTAAGT TGGGTAACGC CAGGGTTTTC CCAGTCACGA CGTTGTAAAA CGACGGCCAG      6294

T                                                                     6295
```

(2) INFORMATION FOR SEQ ID NO:5:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO:5:

```
Met Cys Gln Ser Arg Tyr Leu Leu Phe Leu Ala Thr Leu Ala Leu Leu
 1               5                  10                  15

Asn His Leu Ser Leu Ala Arg Val Ile Pro Val Ser Gly Pro Ala Arg
                20                  25                  30

Cys Leu Ser Gln Ser Arg Asn Leu Leu Lys Thr Thr Asp Asp Met Val
            35                  40                  45

Lys Thr Ala Arg Glu Lys Leu Lys His Tyr Ser Cys Thr Ala Glu Asp
 50                  55                  60

Ile Asp His Glu Asp Ile Thr Arg Asp Gln Thr Ser Thr Leu Lys Thr
 65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala
    210                 215
```

(2) INFORMATION FOR SEQ ID NO:6:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO:6:

```
Met Cys Pro Gln Lys Leu Thr Ile Ser Trp Phe Ala Ile Val Leu Leu
 1               5                  10                  15

Val Ser Pro Leu Met Ala Met Trp Glu Leu Glu Lys Asp Val Tyr Val
                20                  25                  30

Val Glu Val Asp Trp Thr Pro Asp Ala Pro Gly Glu Thr Val Asn Leu
            35                  40                  45
```

-continued

```
Thr Cys Asp Thr Pro Glu Glu Asp Asp Ile Thr Trp Thr Ser Asp Gln
     50                  55                      60

Arg His Gly Val Ile Gly Ser Gly Lys Thr Leu Thr Ile Thr Val Lys
 65                  70                  75                  80

Glu Phe Leu Asp Ala Gly Gln Tyr Thr Cys His Lys Gly Gly Glu Thr
             85                      90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
            115                 120                 125

Glu Ala Pro Asn Tyr Ser Gly Arg Phe Thr Cys Ser Trp Leu Val Gln
            130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
                180                 185                 190

Glu Asp Val Thr Cys Pro Thr Ala Glu Glu Thr Leu Pro Ile Glu Leu
            195                 200                 205

Ala Leu Glu Ala Arg Gln Gln Asn Lys Tyr Glu Asn Tyr Ser Thr Ser
            210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
                260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
            290                 295                 300

Cys Lys Gly Gly Asn Val Cys Val Gln Ala Gln Asp Arg Cys Tyr Asn
305                 310                 315                 320

Ser Ser Cys Ser Lys Trp Ala Cys Val Pro Cys Arg Val Arg Ser
                325                 330                 335
```